US011752099B2

(12) United States Patent
Begovac et al.

(10) Patent No.: US 11,752,099 B2
(45) Date of Patent: Sep. 12, 2023

(54) INJECTABLE AND BIODEGRADABLE POLYMER FORMULATIONS FOR CONTROLLED RELEASE OF BIOACTIVE AGENTS

(71) Applicant: W. L. Gore & Associates, Inc., Newark, DE (US)

(72) Inventors: Paul C. Begovac, Flagstaff, AZ (US); Robert L. Cleek, Flagstaff, AZ (US); Mei Li, Flagstaff, AZ (US)

( * ) Notice: Subject to any disclaimer, the term of this patent is extended or adjusted under 35 U.S.C. 154(b) by 0 days.

(21) Appl. No.: 15/935,692

(22) Filed: Mar. 26, 2018

(65) Prior Publication Data
US 2018/0271779 A1    Sep. 27, 2018

Related U.S. Application Data

(60) Provisional application No. 62/476,900, filed on Mar. 27, 2017.

(51) Int. Cl.
| | | |
|---|---|---|
| *A61K 9/00* | (2006.01) | |
| *A61K 9/51* | (2006.01) | |
| *C08G 64/02* | (2006.01) | |
| *C08G 63/08* | (2006.01) | |
| *A61K 47/34* | (2017.01) | |
| *A61K 47/14* | (2017.01) | |
| *C08G 63/64* | (2006.01) | |
| *A61K 9/50* | (2006.01) | |

(52) U.S. Cl.
CPC .......... *A61K 9/0024* (2013.01); *A61K 9/0051* (2013.01); *A61K 9/5031* (2013.01); *A61K 9/5153* (2013.01); *A61K 47/14* (2013.01); *A61K 47/34* (2013.01); *C08G 63/08* (2013.01); *C08G 63/64* (2013.01); *C08G 64/0208* (2013.01)

(58) Field of Classification Search
CPC .... A61C 27/50; A61C 17/005; A61K 9/0024; A61K 9/0051; A61K 47/6903; A61K 9/5153; A61K 2300/00; A61K 9/0019; A61K 9/0048; A61F 2002/30583; A61L 27/3839; A61L 27/52; A61L 31/16; A61L 17/005; A61L 27/50; A61L 27/54; A61L 2400/06; A61L 2300/604; A61L 31/14; A61L 2300/602; A61P 27/02
See application file for complete search history.

(56) References Cited

U.S. PATENT DOCUMENTS

| | | | | | |
|---|---|---|---|---|---|
| 5,550,178 | A | * | 8/1996 | Desai | A61K 9/1652 424/488 |
| 5,610,266 | A | * | 3/1997 | Buchholz | A61K 47/34 528/354 |
| 5,728,752 | A | | 3/1998 | Scopelianos et al. | |
| 5,824,333 | A | | 10/1998 | Scopelianos et al. | |
| 6,048,947 | A | * | 4/2000 | Oberhoffner | A61L 17/10 525/411 |
| 6,398,761 | B1 | * | 6/2002 | Bills | A61C 9/0026 222/145.5 |
| 6,413,536 | B1 | * | 7/2002 | Gibson | A61K 8/60 264/4.1 |
| 8,039,021 | B2 | | 10/2011 | Royer | |
| 8,784,893 | B2 | | 7/2014 | Daniloff et al. | |
| 9,198,884 | B2 | | 12/2015 | Malmsten et al. | |
| 2003/0223957 | A1 | * | 12/2003 | Schwartz | A61K 9/0048 424/78.38 |
| 2007/0077304 | A1 | | 4/2007 | Luk et al. | |
| 2007/0196415 | A1 | * | 8/2007 | Chen | A61K 9/0024 424/422 |
| 2008/0166411 | A1 | * | 7/2008 | Shah | A61K 9/0019 424/489 |
| 2009/0104241 | A1 | * | 4/2009 | Pacetti | A61L 31/10 424/423 |
| 2012/0283391 | A1 | * | 11/2012 | Venkatraman | A61L 17/06 525/411 |

(Continued)

FOREIGN PATENT DOCUMENTS

| | | |
|---|---|---|
| CN | 103446043 A | 12/2013 |
| EP | 1 731 178 A2 | 12/2006 |
| JP | 2004-511431 A | 4/2004 |
| JP | 2009-510116 A | 3/2009 |
| JP | 2011-500282 A | 1/2011 |
| KR | 10-2004-0058100 A | 7/2004 |
| WO | 02/00137 A1 | 1/2002 |
| WO | 02/26279 A1 | 4/2002 |
| WO | WO02/26270 | 4/2002 |

(Continued)

OTHER PUBLICATIONS

Signma Aldrich. Triethyl citrate. Date retrieved: Mar. 5, 2020. <https://www.sigmaaldrich.com/catalog/product/aldrich/109290?lang=en&region=US>. (Year: 2020).*

(Continued)

*Primary Examiner* — Tracy Liu
(74) *Attorney, Agent, or Firm* — W. L. GORE & ASSOCIATES, INC.; Amy Miller

(57) ABSTRACT

The present disclosure is directed to injectable formulations that include biodegradable polymers based on trimethylene carbonate (TMC) with mole fractions of polylactic acid (PLA) and/or polyglycolic acid (PGA) that are used to deliver a bioactive agent to a targeted site. Excipients such as polyethylene glycol (PEG) may be added to the formulations to reduce the injection force and/or to modulate the release of the bioactive agent. Suitable biodegradable polymers for use in the injectable formulations include D,L-PLA:TMC, D-PLA:TMC, L-PLA:TMC, TMC:PLA:PGA and variations thereof. Additionally, copolymers of TMC and PLA and terpolymers of TMC:PLA:PGA may be formed into nanoparticles and delivered to the target site with an injectable crosslinkable polyethylene glycol system. In at least one embodiment, the injectable formulations are used to treat ocular diseases.

17 Claims, 10 Drawing Sheets

(56) References Cited

U.S. PATENT DOCUMENTS

2013/0059925 A1* 3/2013 Nair .................. A61K 47/34
 514/772.1
2017/0216529 A1* 8/2017 Donovan ............. A61M 5/178

FOREIGN PATENT DOCUMENTS

| WO | 03/41684 A2 | 5/2003 |
|---|---|---|
| WO | WO 2007/041410 A2 | 4/2007 |
| WO | 2018/183224 A2 | 10/2018 |

OTHER PUBLICATIONS

Xinyi Jiang et al: "Solid tumor penetration by integrin-mediated pegylated poly(trimethylene carbonate) nanoparticles loaded with paclitaxel", Biomaterials., vol. 34, No. 6, Dec. 2, 2012 (Dec. 2, 2012), pp. 1739-1746, XP055509418, GB ISSN: 0142-9612, DOI: 10.1016/j.biomaterials.2012.11.016.

International Search Report of PCT/US2018/024416 dated Oct. 10, 2018.

Umeki N et al: "Preparation and evaluation of biodegradable films containing the potent osteogenic compound BFB0261 for localized delivery", International Journal of Pharmaceutics, Elsevier, NL, 1-12 vol. 404, No. 1-2, Feb. 14, 2011 (Feb. 14, 2011), pp. 10-18, XP027575223, ISSN: 0378-5173 [retrieved on Oct. 31, 2010].

Davachi S M et al: 11 Investigating thermal degradation, crystallization and surface behavior of-lactide, glycolide and trimethylene carbonate terpolymers used for medi cal applications 11, A Materials Science and Engineering C, Elsevier Science S.A, CH, vol. 32, No. 2, Oct. 5, 2011 (Oct. 5, 2011), pp. 98-104, XP028 356487, ISSN: 0928-4931, DOI: 10.1016/J.MSEC.2011.10 .001 [retrieved on Oct. 12, 2011].

Gao M et al: 11 Improved poly(d,l-lactide-co-1,3-trimethylenecarbonate)6 copolymer microparticle vehi cles for sustained and controlled del ivery of bioactive basic fibroblast growth factor11, Journal of Bioactive and Compatible Polymers Jul. 19, 2015 Sage Publications Ltd GBR, vol. 30, No. 4, Jul. 19, 2015 (Jul. 19, 2015), pp. 381-396, XP009506787, DOI: 10.1177/0883911515578869.

Partial International Search Report of PCT/US2018/024416 dated Jul. 31, 2018.

Buchholz, B. "Anaylsis and Chracterizaiton of Resorbable DL-lactide-trimethylene carbonate copolyesters*" Journal of Material Science: Material in Medicine 4 (1993) pp. 381-388.

International Preliminary Reporton Patentability received for PCT Patent Application No. PCT/US2018/024416, dated Oct. 10, 2019, 11 pages.

* cited by examiner

INJECTABLE AND BIODEGRADABLE POLYMER FORMULATIONS FOR CONTROLLED RELEASE OF BIOACTIVE AGENTS

FIELD

The present disclosure relates generally to injectable drug delivery systems, and more specifically to biodegradable injectable polymer formulations that permit an extended or sustained release of a bioactive agent at a targeted site to achieve a desired therapeutic effect.

BACKGROUND

There are a variety of acute and chronic conditions, such as ocular disorders, cancers, and inflammatory diseases (e.g., Chron's disease), that may be treated with bioactive agents and other small molecules. For example, some ocular disorders, if left untreated, may lead to partial or even complete vision loss. One prominent chronic ocular disorder is age-related macular degeneration (ARMD), which is the leading cause of blindness among elderly people. Treatment of ARMD is a disease of the posterior segment of the eye which requires long term pharmacological treatment. Topically applied treatments such as eye drops are ineffective at treating diseases of the posterior segment of the eye because the drops cannot significantly penetrate the eye and deliver the bioactive agent to the target site. Direct injection into the eye, using conventional needles and syringes to deliver a biologic agent has been successful, but requires professional training and/or multiple injections to complete treatment.

It is therefore desirable to minimize the number and/or frequency of eye injection treatments needed to deliver therapeutically effective amounts of drug to the ocular tissue sites to treat and/or cure a disease. It is also desirable to minimize the number and/or frequency of injection treatments to tissue sites other than the eye, including the heart, kidneys, or liver, and subcutaneously, as examples, in order to treat and/or cure a disease.

SUMMARY

One embodiment relates to a sustained-release formulation that includes (1) an injectable bioabsorbable copolymer having repeating units of trimethylene carbonate (TMC) and polylactide (PLA), (2) at least 0.5 wt. % of a pharmaceutically acceptable excipient, (3) 1,2,3-triacetoxypropane, and (4) a bioactive agent. The bioactive agent may be incorporated in the injectable bioabsorbable copolymer. In at least one embodiment, the excipient may be polyethylene glycol, a polyxamer, or polyvinyl alcohol. The copolymer may be L-PLA and TMC in a weight ratio of 55:45, D-PLA and TMC in a weight ratio of 55:45, or D,L-PLA and TMC in a weight ratio of 50:50. Additionally, the formulation has a glide force that is 120 N or less. Further, the bioactive agent has a half-life of release from the injectable bioabsorbable copolymer of greater than 30 days.

Another embodiment relates to a sustained-release formulation for treating ophthalmic disease that includes (1) an injectable bioabsorbable copolymer nanoparticle that includes trimethylene carbonate (TMC) and polylactide (PLA) and (2) a cross-linkable polyethylene glycol (PEG). The copolymer may have a PLA:TMC ratio of 75:25. The formulation may also include a solvent. In at least one embodiment, the solvent may be 1,2,3-triacetoxypropane, acetyltributyl citrate, triethyl citrate, tributyl citrate, or acetyl triethyl citrate. Additionally, the formulation has a glide force that is 120 N or less. The bioactive agent is encapsulated in the nanoparticle, and has a half-life of release from the nanoparticle that is greater than 30 days.

A further embodiment relates to an injectable bioactive agent sustained-release formulation that includes a biodegradable polymer comprising a copolymer with repeating units of trimethylene carbonate (TMC) and a bioactive agent incorporated in the biodegradable polymer. The formulation may also include an excipient and/or a solvent. In at least one embodiment, the excipient may be polyethylene glycol, a poloxamer, or polyvinyl alcohol and the solvent may be 1,2,3-triacetoxypropane, acetyltributyl citrate, triethyl citrate, tributyl citrate, or acetyl triethyl citrate. The formulation has a glide force less than about 120 N. The copolymer may include L-PLA and TMC in a weight ratio of 55:45, D-PLA and TMC in a weight ratio of 55:45, or D,L-PLA and TMC in a weight ratio of 50:50. In exemplary embodiments, 80% of the bioactive agent is released at 80% copolymer degradation.

Yet another embodiment relates to an injectable bioactive agent sustained-release formulation that includes a biodegradable polymer including block copolymer with repeating units of trimethylene carbonate (TMC) and a bioactive agent incorporated in the biodegradable polymer. The formulation may also include an excipient and/or a solvent. In at least one embodiment, the excipient may be polyethylene glycol, a poloxamer, or polyvinyl alcohol and the solvent may be 1,2,3-triacetoxypropane, acetyltributyl citrate, triethyl citrate, tributyl citrate, or acetyl triethyl citrate. The formulation has a glide force that is 120 N or less. In some embodiments, the copolymer may include L-PLA and TMC in a weight ratio of 55:45, D-PLA and TMC in a weight ratio of 55:45, or D,L-PLA and TMC in a weight ratio of 50:50. In exemplary embodiments, the retained activity of the bioactive agent is greater than 90% for the duration of release.

A further embodiment relates to an injectable bioactive agent sustained-release formulation that includes a biodegradable polymer including a copolymer with repeating units of trimethylene carbonate (TMC) and a bioactive agent incorporated in the biodegradable polymer. The copolymer has an amorphous segment and crystalline segment. The formulation may also include an excipient and/or a solvent. In at least one embodiment, the excipient may be polyethylene glycol, a poloxamer, or polyvinyl alcohol and the solvent may be 1,2,3-triacetoxypropane, acetyltributyl citrate, triethyl citrate, tributyl citrate, or acetyl triethyl citrate. The formulation has a glide force that is 120 N or less. In some embodiments, the copolymer may include L-PLA and TMC in a weight ratio of 55:45, D-PLA and TMC in a weight ratio of 55:45, or D,L-PLA and TMC in a weight ratio of 50:50.

Another embodiment relates to a sustained-release formulation that includes an injectable bioabsorbable polymer comprising a trimethylene carbonate (TMC)-based polymer, a pharmaceutically acceptable excipient; a solvent selected from 1,2,3-triacetoxypropane, acetyltributyl citrate, triethyl citrate, tributyl citrate, and acetyl triethyl citrate; and a bioactive agent. The TMC-based polymer comprises a) a copolymer comprising repeating units of trimethylene carbonate and lactide, and/or b) a polylactide (PLA), (TMC), polyglycolic acid (PGA) terpolymer, wherein the terpolymer comprises from 3-19 wt. % PGA and wherein the PLA:TMC weight ratio is from 3.25:1 to 0.75:1. The bioactive agent may have a half-life of release from said injectable bioabsorbable polymer of greater than 30 days. The copolymer may have an amorphous segment and crystalline segment. The excipient may be selected from polyethylene glycol, poloxamers, and polyvinyl alcohol. The formulation may have a glide force of 120 N or less. The copolymer may comprise from 45 to 60 wt. % PLA and from 40 to 55 wt. % TMC. In some aspects, the copolymer comprises L-PLA and TMC in a weight ratio of 55:45, D-PLA and TMC in a weight ratio of 55:45, or D,L-PLA and TMC in a weight ratio of 50:50. The terpolymer may have a number average molecular weight from 25,000 to 40,000 g/mol. The terpolymer may have an intrinsic viscosity from 0.90 to 1.2 dL/g. The bioactive agent may be incorporated in said injectable bioabsorbable polymer. The sustained-release formulation may be a delayed-release formulation in vivo or in situ. The formulation may be injected into a tissue site and when injected, the formulation forms a solid/gel structure in the tissue site which allows for delayed release of the bioactive agent.

A further embodiment relates to a sustained-release formulation comprising: an injectable bioabsorbable polymer nanoparticle comprising a trimethylene carbonate (TMC)-based polymer, a cross-linkable polyethylene glycol; and a bioactive agent encapsulated in said nanoparticle. The TMC-based polymer comprises: a) a copolymer comprising repeating units of trimethylene carbonate and lactide, and/or b) a polylactide (PLA), (TMC), polyglycolic acid (PGA) terpolymer, wherein the terpolymer comprises from 3-19 wt. % PGA and wherein the PLA:TMC weight ratio is from 3.25:1 to 0.75:1. The bioactive agent may have a half life of release from said nanoparticle of greater than 30 days. The copolymer may comprise from 60 to 90 wt. % PLA and from 10 to 40 wt. % TMC. The copolymer may have a PLA:TMC weight ratio of 75:25. The terpolymer may have a number average molecular weight from 25,000 to 40,000 g/mol. The terpolymer may have an intrinsic viscosity from 0.90 to 1.2 dL/g. The bioactive agent may be encapsulated in said injectable bioabsorbable polymer. The sustained-release formulation may be a delayed-release formulation in vivo or in situ. The formulation may be injected into a tissue site and when injected, the formulation forms a solid/gel structure in the tissue site which allows for delayed release of the bioactive agent.

BRIEF DESCRIPTION OF THE DRAWINGS

The accompanying drawings are included to provide a further understanding of the disclosure and are incorporated in and constitute a part of this specification, illustrate embodiments, and together with the description serve to explain the principles of the disclosure.

DETAILED DESCRIPTION

Figure 1:
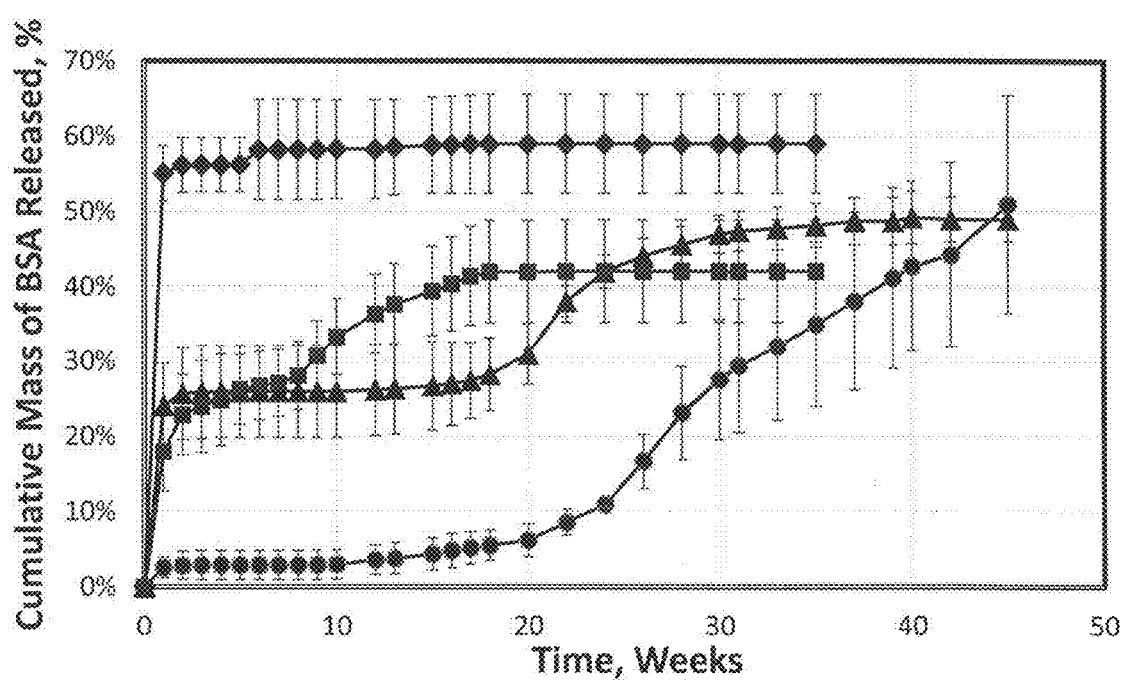
FIG. 1 is a graphical illustration depicting the percent cumulative mass of bovine serum albumin (BSA) that is released over time for the L-PLA:TMC (55:45) formulation of Example 1 (solid triangles), the L-PLA:TMC (55:45) formulation of Example 2 (solid circles), a PLGA low MW formulation (RS752S from Evonik Industries, solid diamonds), and a PLGA high MW formulation (RS756S from Evonik Industries, solid squares). All curves are based on theoretical BSA loading.

Persons skilled in the art will readily appreciate that various aspects of the present disclosure can be realized by any number of methods and apparatus configured to perform the intended functions. It should also be noted that the accompanying figures referred to herein are not necessarily drawn to scale, but may be exaggerated to illustrate various aspects of the present disclosure, and in that regard, the figures should not be construed as limiting. It is to be noted that the terms "TMC-based copolymer", "copolymer", and "polymer" may be used interchangeably herein. Additionally, the term "terpolymer" and "TMC:PLA:PGA" may be used interchangeably and collectively herein. The terpolymer may also be TMC-based. As used herein, "TMC-based polymer" refers to a copolymer or terpolymer having a minimum of 20 weight percent (wt. %) of trimethylene carbonate.

The present disclosure is directed to injectable formulations that include biodegradable polymers based on trimethylene carbonate (TMC) with mole fractions of polylactic acid (PLA) and/or polyglycolic acid (PGA) that are used to deliver a bioactive agent agent to a targeted site. Excipients such as polyethylene glycol (PEG) may be added to the formulations to reduce the injection force and/or to modulate the release of the bioactive agent. Additionally, copolymers of TMC and PLA, and terpolymers of TMC, PLA and PGA may be formed into nanoparticles and delivered to the target site with an injectable crosslinkable polyethylene glycol system. In at least one embodiment, the injectable formulations are used to treat ocular diseases.

The injectable formulations include copolymers that may be a TMC-based copolymer that includes trimethylene carbonate (TMC) monomers. The copolymers may have a number average molecular weight greater than 20,000 g/mol and a solubility greater than about 2 wt. %. Comonomers suitable for use with TMC include, but are not limited to, L-Lactic acid comonomers creating poly(L,Lactic acid-TMC) hereinafter "L-PLA:TMC"; D-Lactic acid comonomers creating poly(D,Lactic acid-TMC) hereinafter "D-PLA:TMC"; and comonomers of L-lactic acid and D-lactic acid and TMC creating Poly(DL,Lactic acid-TMC) hereinafter "D,L-PLA:TMC". Comonomers of lactic acid and glycolic acid and TMC may be used to create a terpolymer, Poly(Lactic and Glycolic acid-TMC), hereinafter "PLA:PGA:TMC". The copolymers may have a weight ratio of D-PLA to TMC of 55% to 45% (55:45) or 75% to 25% (75:25), L-PLA to TMC of 55% to 45% (55:45) or 75% to 25% (75:25), and D,L-PLA to TMC of 50% to 50% (50:50) or 75% to 25% (75:25) (all based on weight). In some aspects, the copolymer may comprise from 45 to 60 wt. % PLA and from 40 to 55 wt. % TMC.

The injectable formulations may include terpolymers instead of or in addition to copolymers. The terpolymer may comprise from 3-19 wt. % PGA and may comprise PLA:TMC in a weight ratio from 3.25:1 to 0.75:1. The terpolymer may have a weight ratio of D-PLA to TMC of 3.25:1 to 0.75:1, L-PLA to TMC of 3.25:1 to 0.75:1, or D,L-PLA to TMC of 3.25:1 to 0.75:1. The terpolymer may have a number average molecular weight of 25,000 to 40,000 g/mol. The TMC-based copolymers and PLA:TMC:PGA terpolymer are both stable and biocompatible, for example with the eye, and may be injected through a small gauge needle (e.g., 25-30 gauge).

Once polymer synthesis is complete, the polymerized copolymer or terpolymer may be put into an injectable solution. In exemplary embodiments, the copolymer or terpolymer is in the form of an injectable liquid which solidifies in the body. Suitable examples of solvents used to place the biodegradable TMC-based polymers and the PLA:TMC:PGA terpolymer into solution include, but are not limited to biocompatible solvents such as triacetin (1,2,3-triacetoxypropane), acetyltributyl citrate, triethyl citrate, tributyl citrate, and acetyl triethyl citrate. It should be appreciated by one of skill in the art that within the scope of the present disclosure, reference to "a" or "the" solvent is intended to include a scope wherein at least one solvent may be used. In some instances, heat may be applied to dissolve the copolymer into solution. Heating copolymers of PLA:TMC to enhance solubility is generally not ideal as the elevated temperature may lead to enhanced degradation of the polymer. Although some degradation of the TMC-based copolymer occurs when it is heated to 100° C., the degradation at 100° C. is not significant enough to exclude the PLA:TMC copolymers described herein from use in the injectable formulation.

In some embodiments, an excipient is added to reduce the injection force and/or to modulate the release of the bioactive agent. In some embodiments, the excipient is included in the formulation in an amount of at least 1 wt. % or at least 5 wt. % of the injectable formulation. Exemplary excipients include biocompatible excipients. Examples include, but are not limited to polyethylene glycol (PEG), poloxamers, and polyvinyl alcohol (PVA). The addition of PEG, for example, enables the injectable formulation to be injected at a lower glide force. Increasing the content of PEG in the injectable formulation may significantly lower the glide force. In some aspects, specifically for the terpolymer, the excipient may be present from 0 to 3 wt. %, e.g., from 0.001 to 3 wt. % or from 1.5 to 2.3 wt. %. In some embodiments, the formulations are injectable at a glide force of 120 N or less, and in other embodiments, less than about 100 N.

It should be appreciated by one of skill in the art that within the scope of the present disclosure, reference to "a" or "the" bioactive agent is intended to include a scope wherein at least one bioactive agent is incorporated into the injectable formulation. "Bioactive agent" as used herein is meant to include a moiety or compound that provides a therapeutic benefit to the patient. Examples of bioactive agents for use in the injectable formulations include, but are not limited to, bioactive agents for wet macular degeneration such as bevacizumab (Avastin®), ranibizumab (Lucentis®), aflibercept (Eylea®), and potential bioactive agents for dry macular degeneration such as lampalizumab. Anti-inflammatory glucocorticoids such as dexamethasone and fluocinolone acetonide may also or alternatively be included in the injectable formulation. Additional bioactive agents are disclosed herein.

In use, the injectable formulation (i.e., TMC-based copolymer or PLA:TMC:PGA terpolymer, bioactive agent, and optional excipient) may be injected into a tissue bed, where it forms a solid mass. The mass may be a solid gel, e.g., not in liquid, solution, or dispersion form. In some aspects, once the injectable formulation is injected, the formulation is embedded within the tissue bed. It is the injection and subsequent formation of a solid mass that may allow for release of the bioactive agent, e.g., delayed release, as described herein. This allows for the release to be in vivo or in situ. The tissue bed may be in the eye, but is not limited to the eye. Additional examples of tissue beds into which the injectable formulation may be injected include, but are not limited to, the heart, kidneys, liver and subcutaneous tissue. In one embodiment, the TMC-based injectable formulation may be in the form of an injectable liquid that solidifies, e.g., is embedded within the eye. The solidified mass, or solid gel structure, (sometimes referred to herein as a depot) exhibits in vivo biocompatibility and tolerability over time. Advantageously, the injectable formulation may be injected into the tissue bed (e.g., an eye) with a small gauge needle (e.g., 25-30 gauge). The TMC-based copolymers or terpolymers act as a release agent for controlling the release of the bioactive agent from the depot. Thus, the bioactive agent is released, over time, into the surrounding tissue bed as the TMC-based polymers biodegrade. The injectable formulation may be formulated such that the bioactive agent is released slowly over time, or it may have an initial low level of release followed by a higher level of release. Alternatively, it may be desirable to have an initial burst release followed by a constant release of bioactive agent for the remainder to the treatment. It is to be noted that the inclusion of an excipient in the injectable formulation increases the rate of release of the bioactive agent. For instance, the greater the mass fraction of PEG that is added to or included in the injectable formulation, the more rapidly the bioactive agent is released from the polymer mass.

The biodegradable injectable polymer formulations are designed to permit an extended or sustained release of a bioactive agent at the targeted site to achieve the desired therapeutic effect. It is desirable that the bioactive agent is released in a manner that treats the underlying disease. As such, the bioactive agent may be released from the TMC-based copolymer or terpolymer over a period of days, weeks, or months. In one embodiment, the bioactive agent has a half-life of release from the bioabsorbable copolymer of greater than about 30 days. In other embodiments, the half-life of release of the bioactive agent is greater than about 6 months or greater than about a year.

Figure 4:
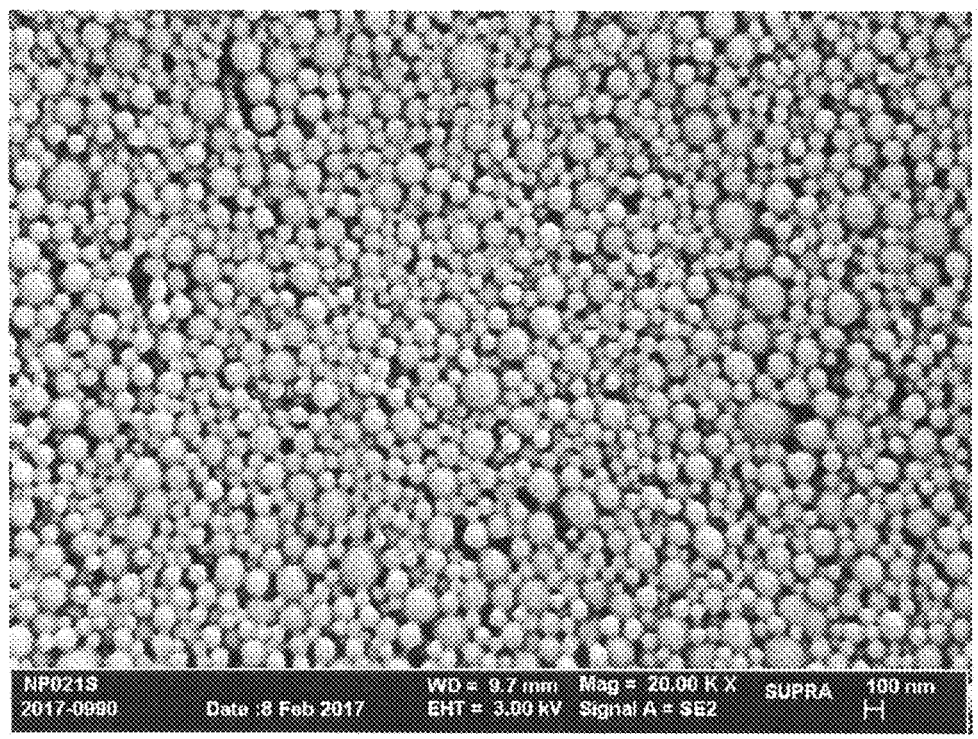
FIG. 4 is a scanning electron micrograph of nanoparticles of L-PLA:TMC having a weight ratio of 75:25 taken at 20,000×.

In another embodiment, the PLA:TMC copolymers or PLA:TMC:PGA terpolymers may be formed into nanoparticles that are substantially spherical in shape. As used herein, "substantially spherical" is meant to denote nanoparticles that are spherical or nearly spherical. Nanoparticles may be utilized for intercellular delivery of the bioactive agent through processes as pinocytosis and phagocytosis. Additionally, the TMC segments may function as an adjuvant to the bioactive agent to improve their performance. FIG. 4 is an SEM of exemplary nanoparticles of a L-PLA:TMC polymer having a weight ratio of 75:25.

The nanoparticles formed from the copolymers of PLA and TMC or from the terpolymers of PLA:TMC:PGA may be contained in an injectable cross-linkable polyethylene glycol (PEG) system. In such an embodiment, a dual syringe set up may be used. For example, a mixture of the nanoparticles and a PEG-amine (pH of 9.0) may be contained within the barrel of one syringe, while a solution of PEG-succinimidyl glutarate (pH 4.0) may be contained within the barrel of the other syringe. The syringes are connected to one another so that the content within each of the barrels can be injected simultaneously or nearly simultaneously. Upon injection, the contents of the two barrels mix and create a rigid hydrogel with the nanoparticles entrapped therein. Without wishing to be limited by theory, it is believed that in certain circumstances this system of combining the gel and nanoparticle provides a scenario in which the gel is used to hide the nanoparticle from the host's immune cells and/or other cascade reactions within the body that may elicit a negative response.

The injectable formulations of the present disclosure may be used in combination with bioactive agents in addition those disclosed above, including, but not limited to, drugs and biologics such as Coagulation Factors, Cytokines, Epigenetic protein families, Growth Factors, Hormones, Peptides, Signal Transduction molecules, and mutations thereof; also including Amino Acids, Vaccines and/or combinations thereof. Bioactive agents further include antibodies, antisense, RNA interference made to the above biologics and their target receptors and mutations of thereof. Additional bioactive agents include Gene Therapy, Primary and Embryonic Stem Cells. Also included in the bioactive agents are antibodies, antisense, RNA interference to Protein Kinases, Esterases, Phosphatases, Ion channels, Proteases, structural proteins, membrane transport proteins, nuclear hormone receptors and/or combinations thereof. Additionally it is to be understood that combinations of bioactive agents as described herein are considered to be within the purview of the present disclosure.

Examples of Coagulation Factors include, but are not limited to: Fibrinogen, Prothrombin, Factor I, Factor V, Factor X, Factor VII, Factor VIII, Factor XI, Factor XIII, Protein C, Platelets, Thromboplastin, and Co-factor of VIIa.

Examples of Cytokines include, but are not limited to: Lymphokines, Interleukins, Chemokines, Monokines, Interferons, and Colony stimulating factors.

Examples of Epigenetic protein families include, but are not limited to: ATPase family AAA domain-containing protein 2 (ATAD2A), ATPase family-AAA domain containing 2B (ATAD2B), ATPase family AAA domain containing-2B (ATAD2B), bromodomain adjacent to zinc finger domain-1A (BAZ1A), bromodomain adjacent to zinc finger domain-1B (BAZ1B), bromodomain adjacent to zinc finger domain-2A (BAZ2A), bromodomain adjacent to zinc finger domain-2A (BAZ2A), bromodomain adjacent to zinc finger domain-2B (BAZ2B), bromodomain-containing protein 1 (BRD1), Bromodomain containing protein 2—1st bromodomain (BRD2), Bromodomain containing protein 2—1st & 2nd bromodomains (BRD2), bromodomain-containing protein 2 isoform 1-bromodomain 2 (BRD2(2)), bromodomain-containing protein 3-bromodomain 1 (BRD3(1)), Bromodomain-containing protein 3—1st bromodomain (BRD3), Bromodomain-containing protein 3—1st & 2nd bromodomains (BRD3), bromodomain-containing protein 3-bromodomain 2 (BRD3(2)), Bromodomain containing protein 4—1st bromodomain (BRD4), bromodomain-containing protein 4 isoform long-bromodomains 1 and 2 (BRD4(1-2)), bromodomain-containing protein 4 isoform long-bromodomain 2 (BRD4(2)), bromodomain-containing protein 4 isoform short (BRD4 (full-length-short-iso.)), Bromodomain containing protein 7 (BRD7), bromodomain containing 8-bromodomain 1 (BRD8(1)), bromodomain containing 8-bromodomain 2 (BRD8(2)), bromodomain-containing protein 9 isoform 1 (BRD9), Bromodomain containing testis-specific—1st bromodomain (BRDT), Bromodomain containing testis-specific—1st & 2nd bromodomains (BRDT), bromodomain testis-specific protein isoform b-bromodomain 2 (BRDT(2)), bromodomain and PHD finger containing-1 (BRPF1), bromodomain and PHD finger containing-3 (BRPF3), bromodomain and PHD finger containing-3 (BRPF3), Bromodomain and WD repeat-containing 3—2nd bromodomain (BRWD3(2)), Cat eye syndrome critical region protein 2 (CECR2), CREB binding protein (CREBBP), E1A binding protein p300 (EP300), EP300 (EP300), nucleosome-remodeling factor subunit BPTF isoform 1 (FALZ), Nucleosome-remodeling factor subunit BPT (FALZ), Euchromatic histone-lysine N-methyltransferase 2 (EHMT2), Histone Acetyltransferase-KAT2A (GCN5L2), Euchromatic histone-lysine N-methyltransferase 1 (EHMT1), Histone-lysine N-methyltransferase MLL (MLL), Polybromo 1—1st bromodomain (PB1(1)), Polybromo 1—2nd bromodomain (PB1(2)), polybromo 1-bromodomain 2 (PBRM1(2)), polybromo 1-bromodomain 5 (PBRM1(5)), Histone acetyltransferase KAT2B (PCAF), PH-interacting protein—1st bromodomain (PHIP(1)), PH-interacting protein—2nd bromodomain (PHIP(2)), Protein kinase C-binding protein 1 (PRKCBP1), Protein arginine N-methyltransferase 3 (PRMT3), SWI/SNF related-matrix associated-actin dependent regulator of chromatin-subfamily a-member 2 (SMARCA2), SWI/SNF related-matrix associated-actin dependent regulator of chromatin-subfamily a-member 4 (SMARCA4), Nuclear body protein-SP110 (SP110), Nuclear body protein-SP140 (SP140), Transcription initiation factor TFIID subunit 1 (TAF1(1-2)), TAF1 RNA polymerase II-TATA box binding protein (TBP)-associated factor-250 kDa-bromodomain 2 (TAF1(2)), Transcription initiation factor TFIID subunit 1-like—1st bromodomain (TAF1L(1)), Transcription initiation factor TFIID subunit 1-like—2nd bromodomain (TAF1L(2)), tripartite motif containing 24 (TRIM24(Bromo.)), tripartite motif containing 24 (TRIM24(PHD-Bromo.)), E3 ubiquitin-protein ligase TRIM33 (TRIM33), tripartite motif containing 33 (TRIM33(PHD-Bromo.)), WD repeat 9—1st bromodomain (WDR9(1)), and WD repeat 9—2nd bromodomain (WDR9(2)).

Examples of growth factors include, but are not limited to: nerve growth factor (NGF), vascular endothelial growth factor (VEGF), platelet-derived growth factor (PDGF), C-fos-induced growth factor (FIGF), platelet-activating factor (PAF), transforming growth factor beta (TGF-β), bone morphogenetic proteins (BMPs), Activin, inhibin, fibroblast growth factors (FGFs), granulocyte-colony stimulating factor (G-CSF), granulocyte-macrophage colony stimulating factor (GM-CSF), glial cell line-derived neurotrophic factor (GDNF), growth differentiation factor-9 (GDF9), epidermal growth factor (EGF), transforming growth factor-α (TGF-α), growth factor (KGF), migration-stimulating factor (MSF), hepatocyte growth factor-like protein (HGFLP), hepatocyte growth factor (HGF), hepatoma-derived growth factor (HDGF), and Insulin-like growth factors.

Examples of Hormones include, but are not limited to: Amino acid derived (such as melatonin and thyroxine), Thyrotropin-releasing hormone, Vasopressin, Insulin, Growth Hormones, Glycoprotein Hormones, Luteinizing Hormone, Follicle-stimulating Hormone, Thyroid-stimulating hormone, Eicosanoids, Arachidonic acid, Lipoxins, Prostaglandins, Steroid, Estrogens, Testosterone, Cortisol, and Progestogens.

Examples of Proteins and Peptides and Signal Transduction molecules include, but are not limited to: Ataxia Telangiectasia Mutated, Tumor Protein p53, Checkpoint kinase 2, breast cancer susceptibility protein, Double-strand break repair protein, DNA repair protein RAD50, Nibrin, p53-binding protein, Mediator of DNA damage checkpoint protein, H2A histone family member X, Microcephalin, C-terminal-binding protein 1, Structural maintenance of chromosomes protein 1A, Cell division cycle 25 homolog A (CDC25A), forkhead box O3 (forkhead box O3), nuclear factor of kappa light polypeptide gene enhancer in B-cells inhibitor, alpha (NFKBIA), nuclear factor (erythroid-derived 2)-like 2 (NFE2L2), Natriuretic peptide receptor A (NPR1), Tumor necrosis factor receptor superfamily, member 11a (TNFRSF11A), v-rel reticuloendotheliosis viral oncogene homolog A (avian) (RELA), Sterol regulatory element binding transcription factor 2 (SREBF2), CREB regulated transcription coactivator 1 (CRTC1), CREB regulated transcription coactivator 2 (CRTC2), X-box binding protein 1 (XBP1), and Catenin beta 1 (cadherin-associated protein or CTNNB1).

Examples of G Protein-Coupled Receptors (GPCR) include, but are not limited to: Adenosine receptor family, Adrenergic receptor family, Angiotensin II receptor, Apelin receptor, Vasopressin receptor family, Brain-specific angiogenesis inhibitor family, Bradykinin receptor family, Bombesin receptor family, Complement component 3a receptor 1, Complement component 5a receptor 1, Calcitonin receptor family, Calcitonin receptor-like family, Calcium-sensing receptor, Cholecystokinin A receptor (CCK1), Cholecystokinin B receptor (CCK2), Chemokine (C-C motif) receptor family, Sphingosine 1-phosphate receptor family, Succinic receptor, Cholinergic receptor family. Chemokine-like receptor family, Cannabinoid receptor family, Corticotropin releasing hormone receptor family, prostaglandin D2 receptor, Chemokine C-X3-C receptor family, Chemokine (C-X-C motif) receptor family, Burkitt lymphoma receptor, Chemokine (C-X-C motif) receptor family, Cysteinyl leukotriene receptor 2 (CYSLT2), chemokine receptor (FY), Dopamine receptor family, G protein-coupled receptor 183 (GPR183), Lysophosphatidic acid receptor family, Endothelin receptor family, Coagulation factor II (thrombin) receptor family, Free fatty acid receptor family, Formylpeptide receptor family, Follicle stimulating hormone receptor (FSHR), gamma-aminobutyric acid (GABA) B receptor, Galanin receptor family, Glucagon receptor, Growth hormone releasing hormone receptor (GHRH), Ghrelin receptor (ghrelin), Growth hormone secretagogue receptor 1b (GHSR1b), Gastric inhibitory polypeptide receptor (GIP), Glucagon-like peptide receptor family, Gonadotropin-releasing hormone receptor (GnRH), pyroglutamylated RFamide peptide receptor (QRFPR), G protein-coupled bile acid receptor 1 (GPBA), Hydroxycarboxylic acid receptor family, Lysophosphatidic acid receptor 4 (LPA4) Lysophosphatidic acid receptor 5 (GPR92), G protein-coupled receptor 79 pseudogene (GPR79), Hydroxycarboxylic acid receptor 1 (HCA1), G-protein coupled receptor (C5L2, FFA4, FFA4, GPER, GPR1, GPR101, GPR107, GPR119, GPR12, GPR123, GPR132, GPR135, GPR139, GPR141, GPR142, GPR143, GPR146, GPR148, GPR149, GPR15, GPR150, GPR151, GPR152, GPR157, GPR161, GPR162, GPR17, GPR171, GPR173, GPR176, GPR18, GPR182, GPR20, GPR22, GPR25, GPR26, GPR27, GPR3, GPR31, GPR32, GPR35, GPR37L1, GPR39, GPR4, GPR45, GPR50, GPR52, GPR55, GPR6, GPR61, GPR65, GPR75, GPR78, GPR83, GPR84, GPR85, GPR88, GPR97, TM7SF1), Metabotropic glutamate receptor family, Gastrin releasing peptide receptor (BB2), Orexin receptor family, Histamine receptor family, 5-hydroxytryptamine receptor family, KISS1-derived peptide receptor (kisspeptin), Leucine-rich repeat-containing G protein-coupled receptor family, horiogonadotropin receptor (LH), Leukotriene B4 receptor (BLT1), Adenylate Cyclase Activating Polypeptide 1 Receptor 1 (mPAC1), Motilin receptor, Melanocortin receptor family, Melanin concentrating hormone receptor 1 (MCH1), Neuropeptide Y1 receptor (Y1), Neuropeptide Y2 receptor (NPY2R), Opioid receptor family, Oxytocin receptor (OT), P2Y Purinoceptor 12 (mP2Y12), P2Y Purinoceptor 6 (P2Y6), Pancreatic polypeptide receptor family, Platelet-activating factor receptor family, Prostaglandin E receptor family, Prostanoid IP1 receptor (IP1), MAS-related GPR, member family, Rhodopsin (Rhodopsin), Relaxin family peptide receptor family, Somatostatin receptor family, Tachykinin receptor family, Melatonin receptor family, Urotensin receptor family, Vasoactive intestinal peptide receptor 1 (mVPAC1), Neuromedin B Receptor (BB1), Neuromedin U receptor 1 (NMU1), Neuropeptides B/W receptor family, Neuropeptide FF receptor 1 (NPFF1), neuropeptide S receptor 1 (NPS receptor), Neuropeptide Y receptor family, Neurotensin receptor 1 (NTS1), Opsin 5 (OPN5), Opioid receptor-like receptor (NOP), Oxoeicosanoid (OXE) receptor 1 (OXE), Oxoglutarate (alpha-ketoglutarate) receptor 1 (OXGR1), Purinergic receptor family, Pyrimidinergic receptor family, Prolactin releasing hormone receptor (PRRP), Prokineticin receptor family, Platelet activating receptor (PAF), Prostaglandin F receptor family, Prostaglandin 12 (prostacyclin) receptor family, Parathyroid hormone receptor family, muscarinic acetylcholine receptors (such as rM4), Prostanoid DP2 receptor (rGPR44), Prokineticin receptor family, Relaxin family peptide receptor family, Secretin receptor (secretin), Frizzled class receptor (Smoothened), trace amine associated receptor family, Tachykinin family, Thromboxane A2 receptor (TP), Thyrotropin-releasing hormone receptor (TRH1), and Thyroid Stimulating Hormone Receptor (TSH).

Examples of nuclear hormone receptors include, but are not limited to: Androgen receptor (AR), Estrogen related receptor alpha (ESRRA), Estrogen receptor 1 (ESR1), Nuclear receptor subfamily 1-group H-member 4 (NR1H4), Nuclear receptor subfamily 3-group C-member 1 (glucocorticoid receptor) (NR3C1), Nuclear receptor subfamily 1-group H-member 3 (Liver X receptor α) (NR1H3), Nuclear receptor subfamily 1-group H-member 2 (Liver X receptor β) (NR1H2), Nuclear receptor subfamily 1-group H-member 2 (Liver X receptor β) (NR1H2), Nuclear receptor subfamily 3-group C-member 2 (Mineralcorticoid receptor) (NR3C2), Peroxisome Proliferator Activated Receptor alpha (PPARA), Peroxisome Proliferator Activated Receptor gamma (PPARG), Peroxisome Proliferator Activated Receptor delta (PPARD), Progesterone receptor α (PGR), Progesterone receptor β (PGR), Retinoic acid receptor-alpha (RARA), Retinoic acid receptor-beta (RARB), Retinoid X receptor-alpha (RXRA), Retinoid X receptor-gamma (RXRG), Thyroid hormone receptor-alpha (THRA), Thyroid hormone receptor-beta (THRB), Retinoic acid-related orphan receptor, Liver X receptor, Farnesoid X receptor, Vitamin D receptor, Pregnane X receptor, Constitutive androstane receptor, Hepatocyte nuclear factor 4, Oestrogen receptor, Oestrogen-related receptor, Glucocortioic receptor, and Nerve growth factor-induced-B, Germ cell nuclear factor.

Examples of membrane transport proteins include, but are not limited to: ATP-binding cassette (ABC) superfamily, solute carrier (SLC) superfamily, multidrug resistance protein 1 (P-glycoprotein), organic anion transporter 1, and and proteins such as EAAT3, EAAC1, EAAT1, GLUT1, GLUT2, GLUT9, GLUT10, rBAT, AE1, NBC1, KNBC, CHED2, BTR1, NABC1, CDPD, SGLT1, SGLT2, NIS, CHT1, NET, DAT, GLYT2, CRTR, BOAT1, SIT1, XT3, y+LAT1, BAT1, NHERF1, NHE6, ASBT, DMT1, DCT1, NRAMP2, NKCC2, NCC, KCC3, NACT, MCT1, MCT8, MCT12, SLD, VGLUT3, THTR1, THTR2, PIT2, GLVR2, OCTN2, URAT1, NCKX1, NCKX5, CIC, PiC, ANT1, ORNT1, AGC1, ARALAR, Citrin, STLN2, aralar2, TPC, MUP1, MCPHA, CACT, GC1, PHC, DTD, CLD, DRA, PDS, Prestin, TAT1, FATP4, ENT3, ZnT2, ZnT10, AT1, NPT2A, NPT2B, HHRH, CST, CDG2F, UGAT, UGTL, UGALT, UGT1, UGT2, FUCT1, CDG2C, NST, PAT2, G6PT1, SPX4, ZIP4, LIV4, ZIP13, LZT-Hs9, FPN1, MTP1, IREG1, RHAG, AIM1, PCFT, FLVCR1, FLVCR2, RFT1, RFT2, RFT3, OATP1B1, OATP1B3, and OATP2A1.

Examples of structural proteins include, but are not limited to: tubulin, heat shock protein, Microtubule-stabilizing proteins, Oncoprotein 18, stathmin, kinesin-8 and kinesin-14 family, Kip3, and Kif18A.

Examples of proteases include, but are not limited to ADAM (a disintegrin and metalloprotease) family.

Examples of Protein kinases include, but are not limited to: AP2 associated kinase, *Homo sapiens* ABL proto-oncogene 1—non-receptor tyrosine-protein kinase family, c-abl oncogene 1 receptor tyrosine kinase family, v-abl Abelson murine leukemia viral oncogene homolog 2, activin A receptor family, chaperone—ABC1 activity of bc1 complex homolog (*S. pombe*) (ADCK3), aarF domain containing kinase 4 (ADCK4), v-akt murine thymoma viral oncogene homolog family, anaplastic lymphoma receptor tyrosine kinase family, protein kinase A family, protein kinase B family, ankyrin repeat and kinase domain containing 1 (ANKK1), NUAK family—SNF1-like kinase, mitogen-activated protein kinase kinase kinase family aurora kinase A (AURKA), aurora kinase B (AURKB), aurora kinase C (AURKC), AXL receptor tyrosine kinase (AXL), BMP2 inducible kinase (BIKE), B lymphoid tyrosine kinase (BLK), bone morphogenetic protein receptor family, BMX non-receptor tyrosine kinase (BMX), v-raf murine sarcoma viral oncogene homolog B1 (BRAF), protein tyrosine kinase 6 (BRK), BR serine/threonine kinase family, Bruton agammaglobulinemia tyrosine kinase (BTK), calcium/calmodulin-dependent protein kinase family, cyclin-dependent kinase family, cyclin-dependent kinase-like family, CHK1 checkpoint homolog (*S. pombe*) (CHEK1), CHK2 checkpoint homolog (*S. pombe*) (CHEK2), Insulin receptor, isoform A (INSR), Insulin receptor, isoform B (INSR), rho-interacting serine/threonine kinase (CIT), v-kit Hardy-Zuckerman 4 feline sarcoma viral oncogene homolog (KIT), CDC-Like Kinase family—Hepatocyte growth factor receptor (MET), Proto-oncogene tyrosine-protein kinase receptor, colony-stimulating factor family receptor, c-src tyrosine kinase (CSK), casein kinase family, megakaryocyte-associated tyrosine kinase (CTK), death-associated protein kinase family, doublecortin-like kinase family, discoidin domain receptor tyrosine kinase family, dystrophia myotonica-protein kinase (DMPK), dual-specificity tyrosine-(Y)-phosphorylation regulated kinase family, epidermal growth factor receptor family, eukaryotic translation initiation factor 2-alpha kinase 1 (EIF2AK1), EPH receptor family, Ephrin type-A receptor family, Ephrin type-B receptor family, v-erb-b2 erythroblastic leukemia viral oncogene homolog family, mitogen-activated protein kinase family, endoplasmic reticulum to nucleus signaling 1 (ERN1), PTK2 protein tyrosine kinase 2 (FAK), fer (fps/fes related) tyrosine kinase (FER). feline sarcoma oncogene (FES), Fibroblast growth factor receptor family, Gardner-Rasheed feline sarcoma viral (v-fgr) oncogene homolog (FGR), fms-related tyrosine kinase family, Fms-related tyrosine kinase family, fyn-related kinase (FRK), FYN oncogene related to SRC, cyclin G associated kinase (GAK), eukaryotic translation initiation factor 2 alpha kinase, Growth hormone receptor. G protein-coupled receptor kinase 1 (GRK1), G protein-coupled receptor kinase family, glycogen synthase kinase family, germ cell associated 2 (haspin) (HASPIN), Hemopoietic cell kinase (HCK), homeodomain interacting protein kinase family, mitogen-activated protein kinase kinase kinase kinase family, hormonally up-regulated Neu-associated kinase (HUNK), intestinal cell (MAK-like) kinase (ICK), Insulin-like growth factor 1 receptor (IGF1R), conserved helix-loop-helix ubiquitous kinase (IKK-alpha), inhibitor of kappa light polypeptide gene enhancer in B-cells—kinase beta family, insulin receptor (INSR), insulin receptor-related receptor (INSRR), interleukin-1 receptor-associated kinase family, IL2-inducible T-cell kinase (ITK), Janus kinase family, Kinase Insert Domain Receptor, v-kit Hardy-Zuckerman 4 feline sarcoma viral oncogene homolog, lymphocyte-specific protein tyrosine kinase (LCK), LIM domain kinase family, serine/threonine kinase family leucine-rich repeat kinase family, v-yes-1 Yamaguchi sarcoma viral related oncogene homolog (LYN), male germ cell-associated kinase (MAK); MAP/microtubule affinity-regulating kinase family such as microtubule associated serine/threonine kinase family, maternal embryonic leucine zipper kinase, c-mer proto-oncogene tyrosine kinase (MERTK), met proto-oncogene (hepatocyte growth factor receptor), MAP kinase interacting serine/threonine kinase family, myosin light chain kinase family, mixed lineage kinase domain-like protein isoform, CDC42 binding protein kinase family, serine/threonine kinase family, macrophage stimulating 1 receptor (c-met-related tyrosine kinase) (MST1R), mechanistic target of rapamycin (serine/threonine kinase) (MTOR), muscle-skeletal-receptor tyrosine kinase (MUSK), myosin light chain kinase family, NIMA (never in mitosis gene a)-related kinase family, serine/threonine-protein kinase NIM1 (NIM1), nemo-like kinase (NLK), oxidative-stress responsive 1 (OSR1), p21 protein (Cdc42/Rac)-activated kinase family, PAS domain containing serine/threonine kinase, Platelet-derived growth factor receptor family, 3-phosphoinositide dependent protein kinase-1 (PDPK1), Calcium-dependent protein kinase 1, phosphorylase kinase gamma family, Phosphatidylinositol 4,5-bisphosphate 3-kinase, phosphoinositide-3-kinase family, phosphatidylinositol 4-kinase family. phosphoinositide kinase, FYVE finger containing, Pim-1 oncogene (PIM1), pim-2 oncogene (PIM2), pim-3 oncogene (PIM3), phosphatidylinositol-4-phosphate 5-kinase family, phosphatidylinositol-5-phosphate 4-kinase family protein kinase, membrane associated tyrosine/threonine 1 (PKMYT1), protein kinase N family, polo-like kinase family, protein kinase C family, protein kinase D family, cGMP-dependent protein kinase family, eukaryotic translation initiation factor 2-alpha kinase 2 (PRKR), X-linked protein kinase (PRKX), Prolactin receptor (PRLR), PRP4 pre-mRNA processing factor 4 homolog B (yeast) (PRP4), PTK2B protein tyrosine kinase 2 beta (PTK2B), SIK family kinase 3 (QSK), v-raf-1 murine leukemia viral oncogene homolog 1 (RAF1), Neurotrophic tyrosine kinase receptor type family, receptor (TNFRSF)-interacting serine-threonine kinase family, dual serine/threonine and tyrosine protein kinase (RIPK5), Rho-associated, coiled-coil containing protein kinase family, c-ros oncogene 1, receptor tyrosine kinase (ROS1), ribosomal protein S6 kinase family, SH3-binding domain kinase 1 (SBK1), serum/glucocorticoid regulated kinase family, Putative uncharacterized serine/threonine-protein kinase (Sugen kinase 110) (SgK110), salt-inducible kinase family, SNF related kinase (SNRK), src-related kinase, SFRS protein kinase family; Spleen tyrosine kinase (SYK) such as TAO kinase family; TANK-binding kinase 1 (TBK1) such as tec protein tyrosine kinase (TEC), testis-specific kinase 1 (TESK1), transforming growth factor, beta receptor family, tyrosine kinase with immunoglobulin-like and EGF-like domains 1 (TIE1), TEK tyrosine kinase, endothelial (TIE2), Angiopoietin-1 receptor (Tie2), tousled-like kinase family, TRAF2 and NCK interacting kinase (TNIK), non-receptor tyrosine kinase family, TNNI3 interacting kinase (TNN13K), transient receptor potential cation channel, testis-specific serine kinase family, TTK protein kinase (TTK), TXK tyrosine kinase (TXK), Tyrosine kinase 2 (TYK2), TYRO3 protein tyrosine kinase (TYRO3), unc-51-like kinase family, phosphatidylinositol 3-kinase, vaccinia related kinase 2 (VRK2), WEE1 homolog family, WNK lysine deficient protein kinase family, v-yes-1 Yamaguchi sarcoma viral oncogene homolog 1 (YES), sterile alpha motif and leucine zipper containing kinase AZK (ZAK), and zeta-chain (TCR) associated protein kinase 70 kDa (ZAP70).

Non-limiting examples of other known biologics include, but are not limited to: Abbosynagis, Abegrin, Actemra, AFP-Cide, Antova, Arzerra, Aurexis, Avastin, Benlysta, Bexxar, Blontress, Bosatria, Campath, CEA-Cide, CEA-Scan, Cimzia, Cyramza, Ektomab, Erbitux, FibriScint, Gazyva, Herceptin, hPAM4-Cide, HumaSPECT, HuMax-CD4, HuMax-EGFr, Humira, HuZAF, Hybri-ceaker, Ilaris, Indimacis-125, Kadcyla, Lemtrada, LeukArrest, Leuko-Scan, Lucentis, Lymphomun, LymphoScan, LymphoStat-B, MabThera, Mycograb, Mylotarg, Myoscint, NeutroSpec, Numax, Nuvion, Omnitarg, Opdivo, Orthoclone OKT3, OvaRex, Panorex, Prolia, Prostascint, Raptiva, Remicade, Removab, Rencarex, ReoPro, Rexomun, Rituxan, RoActemra, Scintimun, Simponi, Simulect, Soliris, Stelara, Synagis, Tactress, Theracim, Theragyn, Theraloc, Tysabri, Vectibix, Verluma, Xolair, Yervoy, Zenapax, and Zevalin and combinations thereof.

Non-limiting examples of known Monoclonal antibodies include, but are not limited to: 3F8, 8H9, Abagovomab, Abciximab, Abituzumab, Abrilumab, Actoxumab, Adalimumab, Adecatumumab, Aducanumab, Afasevikumab, Afelimomab, Afutuzumab, Alacizumab pegol, ALD518, ALD403, Alemtuzumab, Alirocumab, Altumomab pentetate, Amatuximab, AMG 334, Anatumomab mafenatox, Anetumab ravtansine, Anifrolumab, Anrukinzumab, Apolizumab, Arcitumomab, Ascrinvacumab, Aselizumab, Atezolizumab, Atinumab, Atlizumab, Atorolimumab, Avelumab, Bapineuzumab, Basiliximab, Bavituximab, Bectumomab, Begelomab, Belimumab, Benralizumab, Bertilimumab, Besilesomab, Bevacizumab, Bezlotoxumab, Biciromab, Bimagrumab, Bimekizumab, Bivatuzumab mertansine, Bleselumab, Blinatumomab, Blontuvetmab, Blosozumab, Bococizumab, Brazikumab, Brentuximab vedotin, Briakinumab, Brodalumab, Brolucizumab, Brontictuzumab, Burosumab, Cabiralizumab, Canakinumab, Cantuzumab mertansine, Cantuzumab ravtansine, Caplacizumab, Capromab pendetide, Carlumab, Carotuximab, Catumaxomab, cBR96-doxorubicin immunoconjugate, Cedelizumab, Cergutuzumab amunaleukin, Certolizumab pegol, Cetuximab, Citatuzumab bogatox, Cixutumumab, Clazakizumab, Clenoliximab, Clivatuzumab tetraxetan, Codrituzumab, Coltuximab ravtansine, Conatumumab, Concizumab, CR6261, Crenezumab, Crotedumab, Dacetuzumab, Daclizumab, Dalotuzumab, Dapirolizumab pegol, Daratumumab, Dectrekumab, Demcizumab, Denintuzumab mafodotin, Denosumab, Depatuxizumab mafodotin, Derlotuximab biotin, Detumomab, Dinutuximab, Diridavumab, Domagrozumab, Dorlimomab aritox, Drozitumab, Duligotumab, Dupilumab, Durvalumab, Dusigitumab, Ecromeximab, Eculizumab, Edobacomab, Edrecolomab, Efalizumab, Efungumab, Eldelumab, Elgemtumab, Elotuzumab, Elsilimomab, Emactuzumab, Emibetuzumab, Emicizumab, Enavatuzumab, Enfortumab vedotin, Enlimomab pegol, Enoblituzumab, Enokizumab, Enoticumab, Ensituximab, Epitumomab cituxetan, Epratuzumab, Erenumab, Erlizumab, Ertumaxomab, Etaracizumab, Etrolizumab, Evinacumab, Evolocumab, Exbivirumab, Fanolesomab, Faralimomab, Farletuzumab, Fasinumab, FBTA05, Felvizumab, Fezakinumab, Fibatuzumab, Ficlatuzumab, Figitumumab, Firivumab, Flanvotumab, Fletikumab, Fontolizumab, Foralumab, Foravirumab, Fresolimumab, Fulranumab, Futuximab, Galcanezumab, Galiximab, Ganitumab, Gantenerumab, Gavilimomab, Gemtuzumab ozogamicin, Gevokizumab, Girentuximab, Glembatumumab vedotin, Golimumab, Gomiliximab, Guselkumab, Ibalizumab, Ibritumomab tiuxetan, Icrucumab, Idarucizumab, Igovomab, IMA-638, IMAB362, Imalumab, Imciromab, Imgatuzumab, Inclacumab, Indatuximab ravtansine, Indusatumab vedotin, Inebilizumab, Infliximab, Inolimomab, Inotuzumab ozogamicin, Intetumumab, Ipilimumab, Iratumumab, Isatuximab, Itolizumab, Ixekizumab, Keliximab, Labetuzumab, Lambrolizumab, Lampalizumab, Lanadelumab, Landogrozumab, Lapritumumab emtansine, LBR-101/PF0442 g7429, Lebrikizumab, Lemalesomab, Lendalizumab, Lenzilumab, Lerdelimumab, Lexatumumab, Libivirumab, Lifastuzumab vedotin, Ligelizumab, Lilotomab satetraxetan, Lintuzumab, Lirilumab, Lodelcizumab, Lokivetmab, Lorvotuzumab mertansine, Lucatumumab, Lulizumab pegol, Lumiliximab, Lumretuzumab, LY2951742, Mapatumumab, Margetuximab, Maslimomab, Matuzumab, Mavrilimumab, Mepolizumab, Metelimumab, Milatuzumab, Minretumomab, Mirvetuximab soravtansine, Mitumomab, Mogamulizumab, Monalizumab, Morolimumab, Motavizumab, Moxetumomab pasudotox, Muromonab-CD3, Nacolomab tafenatox, Namilumab, Naptumomab estafenatox, Naratuximab emtansine, Narnatumab, Natalizumab, Navicixizumab, Navivumab, Nebacumab, Necitumumab, Nemolizumab, Nerelimomab, Nesvacumab, Nimotuzumab, Nivolumab, Nofetumomab merpentan, Obiltoxaximab, Obinutuzumab, Ocaratuzumab, Ocrelizumab, Odulimomab, Ofatumumab, Olaratumab, Olokizumab, Omalizumab, Onartuzumab, Ontuxizumab, Opicinumab, Oportuzumab monatox, Oregovomab, Orticumab, Otelixizumab, Otlertuzumab, Oxelumab, Ozanezumab, Ozoralizumab, Pagibaximab, Palivizumab, Pamrevlumab, Panitumumab, Pankomab, Panobacumab, Parsatuzumab, Pascolizumab, Pasotuxizumab, Pateclizumab, Patritumab, Pembrolizumab, Pemtumomab, Perakizumab, Pertuzumab, Pexelizumab, Pidilizumab, Pinatuzumab vedotin, Pintumomab, Placulumab, Plozalizumab, Pogalizumab, Polatuzumab vedotin, Ponezumab, Prezalizumab, Priliximab, Pritoxaximab, Pritumumab, PRO 140, Quilizumab, Racotumomab, Radretumab, Rafivirumab, Ralpancizumab, Ramucirumab, Ranibizumab, Raxibacumab, Refanezumab, Regavirumab, Reslizumab, Rilotumumab, Rinucumab, Risankizumab, Rituximab, Rivabazumab pegol, Robatumumab, Roledumab, Romosozumab, Rontalizumab, Rovalpituzumab tesirine, Rovelizumab, Ruplizumab, Sacituzumab govitecan, Samalizumab, Sapelizumab, Sarilumab, Satumomab pendetide, Secukinumab, Seribantumab, Setoxaximab, Sevirumab, SGN-CD19A, SGN-CD33A, Sibrotuzumab, Sifalimumab, Siltuximab, Simtuzumab, Siplizumab, Sirukumab, Sofituzumab vedotin, Solanezumab, Solitomab, Sonepcizumab, Sontuzumab, Stamulumab, Sulesomab, Suvizumab, Tabalumab, Tacatuzumab tetraxetan, Tadocizumab, Talizumab, Tamtuvetmab, Tanezumab, Taplitumomab paptox, Tarextumab, Tefibazumab, Telimomab aritox, Tenatumomab, Teneliximab, Teplizumab, Teprotumumab, Tesidolumab, Tetulomab, Tezepelumab, TGN1412, Ticilimumab, Tigatuzumab, Tildrakizumab, Timolumab, Tisotumab vedotin, TNX-650, Tocilizumab, Toralizumab, Tosatoxumab, Tositumomab, Tovetumab, Tralokinumab, Trastuzumab, Trastuzumab emtansine, TRBS07, Tregalizumab, Tremelimumab, Trevogrumab, Tucotuzumab celmoleukin, Tuvirumab, Ublituximab, Ulocuplumab, Urelumab, Urtoxazumab, Ustekinumab, Utomilumab, Vadastuximab talirine, Vandortuzumab vedotin, Vantictumab, Vanucizumab, Vapaliximab, Varlilumab, Vatelizumab, Vedolizumab, Veltuzumab, Vepalimomab, Vesencumab, Visilizumab, Vobarilizumab, Volociximab, Vorsetuzumab mafodotin, Votumumab, Xentuzumab, Zalutumumab, Zanolimumab, Zatuximab, Ziralimumab, and Zolimomab aritox and combinations thereof.

Examples of vaccines developed for viral diseases include, but are not limited to: Hepatitis A vaccine, Hepatitis B vaccine, Hepatitis E vaccine, HPV vaccine, Influenza vaccine, Japanese encephalitis vaccine, MMR vaccine, MMRV vaccine, Polio vaccine, Rabies vaccine, Rotavirus vaccine, Varicella vaccine, Shingles vaccine, Smallpox vaccine, Yellow Fever vaccine, Adenovirus vaccine, Coxsackie B virus vaccine, Cytomegalovirus vaccine, Dengue vaccine for humans, Eastern Equine encephalitis virus vaccine for humans, Ebola vaccine, Enterovirus 71 vaccine, Epstein-Barr vaccine, Hepatitis C vaccine, HIV vaccine, HTLV-1 T-lymphotropic leukemia vaccine for humans, Marburg virus disease vaccine, Norovirus vaccine, Respiratory syncytial virus vaccine for humans, Severe acute respiratory syndrome (SARS) vaccine, West Nile virus vaccine for humans; Examples of bacterial diseases include but are not limited to: Anthrax vaccines, DPT vaccine, Q fever vaccine, Hib vaccine, Tuberculosis (BCG) vaccine, Meningococcal vaccine, Typhoid vaccine, Pneumococcal conjugate vaccine, Pneumococcal polysaccharide vaccine, Cholera vaccine, Caries vaccine, Ehrlichiosis vaccine, Leprosy vaccine, Lyme disease vaccine, *Staphylococcus aureus* vaccine, *Streptococcus pyogenes* vaccine, Syphilis vaccine, Tularemia vaccine, and *Yersinia pestis* vaccine; Examples of parasitic diseases include, but are not limited to: Malaria vaccine, Schistosomiasis vaccine, Chagas disease vaccine, Hookworm vaccine, Onchocerciasis river blindness vaccine for humans, Trypanosomiasis vaccine, and Visceral leishmaniasis vaccine; Examples of non-infectious diseases include, but are not limited to: Alzheimer's disease amyloid protein vaccine, Breast cancer vaccine, Ovarian cancer vaccine, Prostate cancer vaccine, and Talimogene laherparepvec (T-VEC); also vaccines including, but not limited to the following trade names: ACAM2000, ActHIB, Adacel, Afluria, AFLURIA QUADRIVALENT, Agriflu, BCG Vaccine, BEXSERO, Biothrax, Boostrix, Cervarix, Comvax, DAPTACEL, DECAVAC, Engerix-B, FLUAD, Fluarix, Fluarix Quadrivalent, Flublok, Flucelvax, Flucelvax Quadrivalent, FluLaval, FluMist, FluMist Quadrivalent, Fluvirin, Fluzone Quadrivalent, Fluzone, Fluzone High-Dose and Fluzone Intradermal, Gardasil, Gardasil 9, Havrix, Hiberix, Imovax, Infanrix, IPOL, Ixiaro, JE-Vax, KINRIX, Menactra, MenHibrix, Menomune-A/C/Y/W-135, Menveo, M-M-R II, M-M-Vax, Pediarix, PedvaxHIB, Pentacel, Pneumovax 23, Poliovax, Prevnar, Prevnar 13, ProQuad, Quadracel, Quadrivalent, RabAvert, Recombivax HB, ROTARIX, RotaTeq, TENIVAC, TICE BCG, Tripedia, TRUMENBA, Twinrix, TYPHIM Vi, VAQTA, Varivax, Vaxchora, Vivotif, YF-Vax, Zostavax, and combinations thereof.

Examples of injectable drugs include, but are not limited to: Ablavar (Gadofosveset Trisodium Injection), Abarelix Depot, Abobotulinumtoxin A Injection (Dysport), ABT-263, ABT-869, ABX-EFG, Accretropin (Somatropin Injection), Acetadote (Acetylcysteine Injection), Acetazolamide Injection (Acetazolamide Injection), Acetylcysteine Injection (Acetadote), Actemra (Tocilizumab Injection), Acthrel (Corticorelin Ovine Triflutate for Injection), Actummune, Activase, Acyclovir for Injection (Zovirax Injection), Adacel, Adalimumab, Adenoscan (Adenosine Injection), Adenosine Injection (Adenoscan), Adrenaclick, AdreView (Iobenguane 1123 Injection for Intravenous Use), Afluria, Ak-Fluor (Fluorescein Injection), Aldurazyme (Laronidase), Alglucerase Injection (Ceredase), Alkeran Injection (Melphalan Hcl Injection), Allopurinol Sodium for Injection (Aloprim), Aloprim (Allopurinol Sodium for Injection), Alprostadil, Alsuma (Sumatriptan Injection), ALTU-238, Amino Acid Injections, Aminosyn, Apidra, Apremilast, Alprostadil Dual Chamber System for Injection (Caverject Impulse), AMG 009, AMG 076, AMG 102, AMG 108, AMG 114, AMG 162, AMG 220, AMG 221, AMG 222, AMG 223, AMG 317, AMG 379, AMG 386, AMG 403, AMG 477, AMG 479, AMG 517, AMG 531, AMG 557, AMG 623, AMG 655, AMG 706, AMG 714, AMG 745, AMG 785, AMG 811, AMG 827, AMG 837, AMG 853, AMG 951, Amiodarone HCl Injection (Amiodarone HCl Injection), Amobarbital Sodium Injection (Amytal Sodium), Amytal Sodium (Amobarbital Sodium Injection), Anakinra, Anti-Abeta, Anti-Beta7, Anti-Beta20, Anti-CD4, Anti-CD20, Anti-CD40, Anti-IFNalpha, Anti-IL13, Anti-OX40L, Anti-oxLDS, Anti-NGF, Anti-NRP1, Arixtra, Amphadase (Hyaluronidase Inj), Ammonul (Sodium Phenylacetate and Sodium Benzoate Injection), Anaprox, Anzemet Injection (Dolasetron Mesylate Injection), Apidra (Insulin Glulisine [rDNA origin] Inj), Apomab, Aranesp (darbepoetin alfa), Argatroban (Argatroban Injection), Arginine Hydrochloride Injection (R-Gene 10, Aristocort, Aristospan, Arsenic Trioxide Injection (Trisenox), Articane HCl and Epinephrine Injection (Septocaine), Arzerra (Ofatumumab Injection), Asclera (Polidocanol Injection), Ataluren, Ataluren-DMD, Atenolol Inj (Tenormin I.V. Injection), Atracurium Besylate Injection (Atracurium Besylate Injection), Avastin, Azactam Injection (Aztreonam Injection), Azithromycin (Zithromax Injection), Aztreonam Injection (Azactam Injection), Baclofen Injection (Lioresal Intrathecal), Bacteriostatic Water (Bacteriostatic Water for Injection), Baclofen Injection (Lioresal Intrathecal), Bal in Oil Ampules (Dimercarprol Injection), BayHepB, BayTet, Benadryl, Bendamustine Hydrochloride Injection (Treanda), Benztropine Mesylate Injection (Cogentin), Betamethasone Injectable Suspension (Celestone Soluspan), Bexxar, Bicillin C-R 900/300 (Penicillin G Benzathine and Penicillin G Procaine Injection), Blenoxane (Bleomycin Sulfate Injection), Bleomycin Sulfate Injection (Blenoxane), Boniva Injection (Ibandronate Sodium Injection), Botox Cosmetic (OnabotulinumtoxinA for Injection), BR3-FC, Bravelle (Urofollitropin Injection), Bretylium (Bretylium Tosylate Injection), Brevital Sodium (Methohexital Sodium for Injection), Brethine, Briobacept, BTT-1023, Bupivacaine HCl, Byetta, Ca-DTPA (Pentetate Calcium Trisodium Inj), Cabazitaxel Injection (Jevtana), Caffeine Alkaloid (Caffeine and Sodium Benzoate Injection), Calcijex Injection (Calcitrol), Calcitrol (Calcijex Injection), Calcium Chloride (Calcium Chloride Injection 10%), Calcium Disodium Versenate (Edetate Calcium Disodium Injection), Campath (Altemtuzumab), Camptosar Injection (Irinotecan Hydrochloride), Canakinumab Injection (Ilaris), Capastat Sulfate (Capreomycin for Injection), Capreomycin for Injection (Capastat Sulfate), Cardiolite (Prep kit for Technetium Tc99 Sestamibi for Injection), Carticel, Cathflo, Cefazolin and Dextrose for Injection (Cefazolin Injection), Cefepime Hydrochloride, Cefotaxime, Ceftriaxone, Cerezyme, Carnitor Injection, Caverject, Celestone Soluspan, Celsior, Cerebyx (Fosphenytoin Sodium Injection), Ceredase (Alglucerase Injection), Ceretec (Technetium Tc99m Exametazime Injection), Certolizumab, CF-101, Chloramphenicol Sodium Succinate (Chloramphenicol Sodium Succinate Injection), Chloramphenicol Sodium Succinate Injection (Chloramphenicol Sodium Succinate), Cholestagel (Colesevelam HCL), Choriogonadotropin Alfa Injection (Ovidrel), Cimzia, Cisplatin (Cisplatin Injection), Clolar (Clofarabine Injection), Clomiphine Citrate, Clonidine Injection (Duraclon), Cogentin (Benztropine Mesylate Injection), Colistimethate Injection (Coly-Mycin M), Coly-Mycin M (Colistimethate Injection), Compath, Conivaptan Hcl Injection (Vaprisol), Conjugated Estrogens for Injection (Premarin Injection), Copaxone, Corticorelin Ovine Triflutate for Injection (Acthrel), Corvert (Ibutilide Fumarate Injection), Cubicin (Daptomycin Injection), CF-101, Cyanokit (Hydroxocobalamin for Injection), Cytarabine Liposome Injection (DepoCyt), Cyanocobalamin, Cytovene (ganciclovir), D.H.E. 45, Dacetuzumab, Dacogen (Decitabine Injection), Dalteparin, Dantrium IV (Dantrolene Sodium for Injection), Dantrolene Sodium for Injection (Dantrium IV), Daptomycin Injection (Cubicin), Darbepoietin Alfa, DDAVP Injection (Desmopressin Acetate Injection), Decavax, Decitabine Injection (Dacogen), Dehydrated Alcohol (Dehydrated Alcohol Injection), Denosumab Injection (Prolia), Delatestryl, Delestrogen, Delteparin Sodium, Depacon (Valproate Sodium Injection), Depo Medrol (Methylprednisolone Acetate Injectable Suspension), DepoCyt (Cytarabine Liposome Injection), DepoDur (Morphine Sulfate XR Liposome Injection), Desmopressin Acetate Injection (DDAVP Injection), Depo-Estradiol, Depo-Provera 104 mg/ml, Depo-Provera 150 mg/ml, Depo-Testosterone, Dexrazoxane for Injection, Intravenous Infusion Only (Totect), Dextrose/Electrolytes, Dextrose and Sodium Chloride Inj (Dextrose 5% in 0.9% Sodium Chloride), Dextrose, Diazepam Injection (Diazepam Injection), Digoxin Injection (Lanoxin Injection), Dilaudid-HP (Hydromorphone Hydrochloride Injection), Dimercarprol Injection (Bal in Oil Ampules), Diphenhydramine Injection (Benadryl Injection), Dipyridamole Injection (Dipyridamole Injection), DMOAD, Docetaxel for Injection (Taxotere), Dolasetron Mesylate Injection (Anzemet Injection), Doribax (Doripenem for Injection), Doripenem for Injection (Doribax), Doxercalciferol Injection (Hectorol Injection), Doxil (Doxorubicin Hcl Liposome Injection), Doxorubicin Hcl Liposome Injection (Doxil), Duraclon (Clonidine Injection), Duramorph (Morphine Injection), Dysport (Abobotulinumtoxin A Injection), Ecallantide Injection (Kalbitor), EC-Naprosyn (naproxen), Edetate Calcium Disodium Injection (Calcium Disodium Versenate), Edex (Alprostadil for Injection), Engerix, Edrophonium Injection (Enlon), Eliglustat Tartate, Eloxatin (Oxaliplatin Injection), Emend Injection (Fosaprepitant Dimeglumine Injection), Enalaprilat Injection (Enalaprilat Injection), Enlon (Edrophonium Injection), Enoxaparin Sodium Injection (Lovenox), Eovist (Gadoxetate Disodium Injection), Enbrel (etanercept), Enoxaparin, Epicel, Epinepherine, Epipen, Epipen Jr., Epratuzumab, Erbitux, Ertapenem Injection (Invanz), Erythropoieten, Essential Amino Acid Injection (Nephramine), Estradiol Cypionate, Estradiol Valerate, Etanercept, Exenatide Injection (Byetta), Evlotra, Fabrazyme (Adalsidase beta), Famotidine Injection, FDG (Fludeoxyglucose F 18 Injection), Feraheme (Ferumoxytol Injection), Feridex I.V. (Ferumoxides Injectable Solution), Fertinex, Ferumoxides Injectable Solution (Feridex I.V.), Ferumoxytol Injection (Feraheme), Flagyl Injection (Metronidazole Injection), Fluarix, Fludara (Fludarabine Phosphate), Fludeoxyglucose F 18 Injection (FDG), Fluorescein Injection (Ak-Fluor), Follistim AQ Cartridge (Follitropin Beta Injection), Follitropin Alfa Injection (Gonal-f RFF), Follitropin Beta Injection (Follistim AQ Cartridge), Folotyn (Pralatrexate Solution for Intravenous Injection), Fondaparinux, Forteo (Teriparatide (rDNA origin) Injection), Fostamatinib, Fosaprepitant Dimeglumine Injection (Emend Injection), Foscarnet Sodium Injection (Foscavir), Foscavir (Foscarnet Sodium Injection), Fosphenytoin Sodium Injection (Cerebyx), Fospropofol Disodium Injection (Lusedra), Fragmin, Fuzeon (enfuvirtide), GA101, Gadobenate Dimeglumine Injection (Multihance), Gadofosveset Trisodium Injection (Ablavar), Gadoteridol Injection Solution (ProHance), Gadoversetamide Injection (OptiMARK), Gadoxetate Disodium Injection (Eovist), Ganirelix (Ganirelix Acetate Injection), Gardasil, GC1008, GDFD, Gemtuzumab Ozogamicin for Injection (Mylotarg), Genotropin, Gentamicin Injection, GENZ-112638, Golimumab Injection (Simponi Injection), Gonal-f RFF (Follitropin Alfa Injection), Granisetron Hydrochloride (Kytril Injection), Gentamicin Sulfate, Glatiramer Acetate, Glucagen, Glucagon, HAE1, Haldol (Haloperidol Injection), Havrix, Hectorol Injection (Doxercalciferol Injection), Hedgehog Pathway Inhibitor, Heparin, Herceptin, hG-CSF, Humalog, Human Growth Hormone, Humatrope, HuMax, Humegon, Humira, Humulin, Ibandronate Sodium Injection (Boniva Injection), Ibuprofen Lysine Injection (NeoProfen), Ibutilide Fumarate Injection (Corvert), Idamycin PFS (Idarubicin Hydrochloride Injection), Idarubicin Hydrochloride Injection (Idamycin PFS), Ilaris (Canakinumab Injection), Imipenem and Cilastatin for Injection (Primaxin I.V.), Imitrex, Incobotulinumtoxin A for Injection (Xeomin), Increlex (Mecasermin [rDNA origin] Injection), Indocin IV (Indomethacin Inj), Indomethacin Inj (Indocin IV), Infanrix, Innohep, Insulin, Insulin Aspart [rDNA origin] Inj (NovoLog), Insulin Glargine [rDNA origin] Injection (Lantus), Insulin Glulisine [rDNA origin] Inj (Apidra), Interferon alfa-2b, Recombinant for Injection (Intron A), Intron A (Interferon alfa-2b, Recombinant for Injection), Invanz (Ertapenem Injection), Invega Sustenna (Paliperidone Palmitate Extended-Release Injectable Suspension), Invirase (saquinavir mesylate), Iobenguane 1123 Injection for Intravenous Use (AdreView), Iopromide Injection (Ultravist), Ioversol Injection (Optiray Injection), Iplex (Mecasermin Rinfabate [rDNA origin] Injection), Iprivask, Irinotecan Hydrochloride (Camptosar Injection), Iron Sucrose Injection (Venofer), Istodax (Romidepsin for Injection), Itraconazole Injection (Sporanox Injection), Jevtana (Cabazitaxel Injection), Jonexa, Kalbitor (Ecallantide Injection), KCL in D5NS (Potassium Chloride in 5% Dextrose and Sodium Chloride Injection), KCL in D5W, KCL in NS, Kenalog 10 Injection (Triamcinolone Acetonide Injectable Suspension), Kepivance (Palifermin), Keppra Injection (Levetiracetam), Keratinocyte, KFG, Kinase Inhibitor, Kineret (Anakinra), Kinlytic (Urokinase Injection), Kinrix, Klonopin (clonazepam), Kytril Injection (Granisetron Hydrochloride), lacosamide Tablet and Injection (Vimpat), Lactated Ringer's, Lanoxin Injection (Digoxin Injection), Lansoprazole for Injection (Prevacid I.V.), Lantus, Leucovorin Calcium (Leucovorin Calcium Injection), Lente (L), Leptin, Levemir, Leukine Sargramostim, Leuprolide Acetate, Levothyroxine, Levetiracetam (Keppra Injection), Lovenox, Levocarnitine Injection (Carnitor Injection), Lexiscan (Regadenoson Injection), Lioresal Intrathecal (Baclofen Injection), Liraglutide [rDNA] Injection (Victoza), Lovenox (Enoxaparin Sodium Injection), Lucentis (Ranibizumab Injection), Lumizyme, Lupron (Leuprolide Acetate Injection), Lusedra (Fospropofol Disodium Injection), Maci, Magnesium Sulfate (Magnesium Sulfate Injection), Mannitol Injection (Mannitol IV), Marcaine (Bupivacaine Hydrochloride and Epinephrine Injection), Maxipime (Cefepime Hydrochloride for Injection), MDP Multidose Kit of Technetium Injection (Technetium Tc99m Medronate Injection), Mecasermin [rDNA origin] Injection (Increlex), Mecasermin Rinfabate [rDNA origin] Injection (Iplex), Melphalan Hcl Injection (Alkeran Injection), Methotrexate, Menactra, Menopur (Menotropins Injection), Menotropins for Injection (Repronex), Methohexital Sodium for Injection (Brevital Sodium), Methyldopate Hydrochloride Injection, Solution (Methyldopate Hcl), Methylene Blue (Methylene Blue Injection), Methylprednisolone Acetate Injectable Suspension (Depo Medrol), MetMab, Metoclopramide Injection (Reglan Injection), Metrodin (Urofollitropin for Injection), Metronidazole Injection (Flagyl Injection), Miacalcin, Midazolam (Midazolam Injection), Mimpara (Cinacalet), Minocin Injection (Minocycline Inj), Minocycline Inj (Minocin Injection), Mipomersen, Mitoxantrone for Injection Concentrate (Novantrone), Morphine Injection (Duramorph), Morphine Sulfate XR Liposome Injection (DepoDur), Morrhuate Sodium (Morrhuate Sodium Injection), Motesanib, Mozobil (Plerixafor Injection), Multihance (Gadobenate Dimeglumine Injection), Multiple Electrolytes and Dextrose Injection, Multiple Electrolytes Injection, Mylotarg (Gemtuzumab Ozogamicin for Injection), Myozyme (Alglucosidase alfa), Nafcillin Injection (Nafcillin Sodium), Nafcillin Sodium (Nafcillin Injection), Naltrexone XR Inj (Vivitrol), Naprosyn (naproxen), NeoProfen (Ibuprofen Lysine Injection), Nandrol Decanoate, Neostigmine Methylsulfate (Neostigmine Methylsulfate Injection), NEO-GAA, NeoTect (Technetium Tc 99m Depreotide Injection), Nephramine (Essential Amino Acid Injection), Neulasta (pegfilgrastim), Neupogen (Filgrastim), Novolin, Novolog, NeoRecormon, Neutrexin (Trimetrexate Glucuronate Inj), NPH (N), Nexterone (Amiodarone HCl Injection), Norditropin (Somatropin Injection), Normal Saline (Sodium Chloride Injection), Novantrone (Mitoxantrone for Injection Concentrate), Novolin 70/30 Innolet (70% NPH, Human Insulin Isophane Suspension and 30% Regular, Human Insulin Injection), NovoLog (Insulin Aspart [rDNA origin] Inj), Nplate (romiplostim), Nutropin (Somatropin (rDNA origin) for Inj), Nutropin AQ, Nutropin Depot (Somatropin (rDNA origin) for Inj), Octreotide Acetate Injection (Sandostatin LAR), Ocrelizumab, Ofatumumab Injection (Arzerra), Olanzapine Extended Release Injectable Suspension (Zyprexa Relprew), Omnitarg, Omnitrope (Somatropin [rDNA origin] Injection), Ondansetron Hydrochloride Injection (Zofran Injection), OptiMARK (Gadoversetamide Injection), Optiray Injection (Ioversol Injection), Orencia, Osmitrol Injection in Aviva (Mannitol Injection in Aviva Plastic Vessel 250), Osmitrol Injection in Viaflex (Mannitol Injection in Viaflex Plastic Vessel 250), Osteoprotegrin, Ovidrel (Choriogonadotropin Alfa Injection), Oxacillin (Oxacillin for Injection), Oxaliplatin Injection (Eloxatin), Oxytocin Injection (Pitocin), Paliperidone Palmitate Extended-Release Injectable Suspension (Invega Sustenna), Pamidronate Disodium Injection (Pamidronate Disodium Injection), Panitumumab Injection for Intravenous Use (Vectibix), Papaverine Hydrochloride Injection (Papaverine Injection), Papaverine Injection (Papaverine Hydrochloride Injection), Parathyroid Hormone, Paricalcitol Injection Fliptop Vial (Zemplar Injection), PARP Inhibitor, Pediarix, PEGIntron, Peginterferon, Pegfilgrastim, Penicillin G Benzathine and Penicillin G Procaine, Pentetate Calcium Trisodium Inj (Ca-DTPA), Pentetate Zinc Trisodium Injection (Zn-DTPA), Pepcid Injection (Famotidine Injection), Pergonal, Pertuzumab, Phentolamine Mesylate (Phentolamine Mesylate for Injection), Physostigmine Salicylate (Physostigmine Salicylate (injection)), Physostigmine Salicylate (injection) (Physostigmine Salicylate), Piperacillin and Tazobactam Injection (Zosyn), Pitocin (Oxytocin Injection), Plasma-Lyte 148 (Multiple Electrolytes Inj), Plasma-Lyte 56 and Dextrose (Multiple Electrolytes and Dextrose Injection in Viaflex, Plastic Vessel 250), PlasmaLyte, Plerixafor Injection (Mozobil), Polidocanol Injection (Asclera), Potassium Chloride, Pralatrexate Solution for Intravenous Injection (Folotyn), Pramlintide Acetate Injection (Symlin), Premarin Injection (Conjugated Estrogens for Injection), Prep kit for Technetium Tc99 Sestamibi for Injection (Cardiolite), Prevacid I.V. (Lansoprazole for Injection), Primaxin I.V. (Imipenem and Cilastatin for Injection), Prochymal, Procrit, Progesterone, ProHance (Gadoteridol Injection Solution), Prolia (Denosumab Injection), Promethazine HCl Injection (Promethazine Hydrochloride Injection), Propranolol Hydrochloride Injection (Propranolol Hydrochloride Injection), Quinidine Gluconate Injection (Quinidine Injection), Quinidine Injection (Quinidine Gluconate Injection), R-Gene 10 (Arginine Hydrochloride Injection), Ranibizumab Injection (Lucentis), Ranitidine Hydrochloride Injection (Zantac Injection), Raptiva, Reclast (Zoledronic Acid Injection), Recombivarix HB, Regadenoson Injection (Lexiscan), Reglan Injection (Metoclopramide Injection), Remicade, Renegel, Renvela (Sevelamer Carbonate), Repronex (Menotropins for Injection), Retrovir IV (Zidovudine Injection), rhApo2L/TRAIL, Ringer's and 5% Dextrose Injection (Ringers in Dextrose), Ringer's Injection (Ringers Injection), Rituxan, Rituximab, Rocephin (ceftriaxone), Rocuronium Bromide Injection (Zemuron), Roferon-A (interferon alfa-2a), Romazicon (flumazenil), Romidepsin for Injection (Istodax), Saizen (Somatropin Injection), Sandostatin LAR (Octreotide Acetate Injection), Sclerostin Ab, Sensipar (cinacalcet), Sensorcaine (Bupivacaine HCl Injections), Septocaine (Articane HCl and Epinephrine Injection), Serostim LQ (Somatropin (rDNA origin) Injection), Simponi Injection (Golimumab Injection), Sodium Acetate (Sodium Acetate Injection), Sodium Bicarbonate (Sodium Bicarbonate 5% Injection), Sodium Lactate (Sodium Lactate Injection in AVIVA), Sodium Phenylacetate and Sodium Benzoate Injection (Ammonul), Somatropin (rDNA origin) for Inj (Nutropin), Sporanox Injection (Itraconazole Injection), Stelara Injection (Ustekinumab), Stemgen, Sufenta (Sufentanil Citrate Injection), Sufentanil Citrate Injection (Sufenta), Sumavel, Sumatriptan Injection (Alsuma), Symlin, Symlin Pen, Systemic Hedgehog Antagonist, Synvisc-One (Hylan G-F 20 Single Intra-articular Injection), Tarceva, Taxotere (Docetaxel for Injection), Technetium Tc 99m, Telavancin for Injection (Vibativ), Temsirolimus Injection (Torisel), Tenormin I.V. Injection (Atenolol Inj), Teriparatide (rDNA origin) Injection (Forteo), Testosterone Cypionate, Testosterone Enanthate, Testosterone Propionate, Tev-Tropin (Somatropin, rDNA Origin, for Injection), tgAAC94, Thallous Chloride, Theophylline, Thiotepa (Thiotepa Injection), Thymoglobulin (Anti-Thymocyte Globulin (Rabbit), Thyrogen (Thyrotropin Alfa for Injection), Ticarcillin Disodium and Clavulanate Potassium Galaxy (Timentin Injection), Tigan Injection (Trimethobenzamide Hydrochloride Injectable), Timentin Injection (Ticarcillin Disodium and Clavulanate Potassium Galaxy), TNKase, Tobramycin Injection (Tobramycin Injection), Tocilizumab Injection (Actemra), Torisel (Temsirolimus Injection), Totect (Dexrazoxane for Injection, Intravenous Infusion Only), Trastuzumab-DM1, Travasol (Amino Acids (Injection)), Treanda (Bendamustine Hydrochloride Injection), Trelstar (Triptorelin Pamoate for Injectable Suspension), Triamcinolone Acetonide, Triamcinolone Diacetate, Triamcinolone Hexacetonide Injectable Suspension (Aristospan Injection 20 mg), Triesence (Triamcinolone Acetonide Injectable Suspension), Trimethobenzamide Hydrochloride Injectable (Tigan Injection), Trimetrexate Glucuronate Inj (Neutrexin), Triptorelin Pamoate for Injectable Suspension (Trelstar), Twinject, Trivaris (Triamcinolone Acetonide Injectable Suspension), Trisenox (Arsenic Trioxide Injection), Twinrix, Typhoid Vi, Ultravist (Iopromide Injection), Urofollitropin for Injection (Metrodin), Urokinase Injection (Kinlytic), Ustekinumab (Stelara Injection), Ultralente (U), Valium (diazepam), Valproate Sodium Injection (Depacon), Valtropin (Somatropin Injection), Vancomycin Hydrochloride (Vancomycin Hydrochloride Injection), Vancomycin Hydrochloride Injection (Vancomycin Hydrochloride), Vaprisol (Conivaptan Hcl Injection), VAQTA, Vasovist (Gadofosveset Trisodium Injection for Intravenous Use), Vectibix (Panitumumab Injection for Intravenous Use), Venofer (Iron Sucrose Injection), Verteporfin Inj (Visudyne), Vibativ (Telavancin for Injection), Victoza (Liraglutide [rDNA] Injection), Vimpat (lacosamide Tablet and Injection), Vinblastine Sulfate (Vinblastine Sulfate Injection), Vincasar PFS (Vincristine Sulfate Injection), Victoza, Vincristine Sulfate (Vincristine Sulfate Injection), Visudyne (Verteporfin Inj), Vitamin B-12, Vivitrol (Naltrexone XR Inj), Voluven (Hydroxyethyl Starch in Sodium Chloride Injection), Xeloda, Xenical (orlistat), Xeomin (Incobotulinumtoxin A for Injection), Xolair, Zantac Injection (Ranitidine Hydrochloride Injection), Zemplar Injection (Paricalcitol Injection Fliptop Vial), Zemuron (Rocuronium Bromide Injection), Zenapax (daclizumab), Zevalin, Zidovudine Injection (Retrovir IV), Zithromax Injection (Azithromycin), Zn-DTPA (Pentetate Zinc Trisodium Injection), Zofran Injection (Ondansetron Hydrochloride Injection), Zingo, Zoledronic Acid for Inj (Zometa), Zoledronic Acid Injection (Reclast), Zometa (Zoledronic Acid for Inj), Zosyn (Piperacillin and Tazobactam Injection), Zyprexa Relprevv (Olanzapine Extended Release Injectable Suspension) and combinations thereof.

Non-limiting examples are provided below.

EXAMPLES

Polymer Synthesis

The bioabsorbable polymers identified in the Examples were synthesized according to the methodologies described in "Analysis and characterization of resorbable DL-lactide trimethylene carbonate copolyesters", Journal of Material Science: Materials in Medicine 4(1993) pp. 381-88.

Example 1

This example describes the copolymer L-PLA:TMC in a weight ratio of 55:45. Table 1 shows the characterization data for the composition in this example.

Inherent viscosity (IV) was measured using a Cannon MiniPV-HX Automatic Viscometer with hexafluoroisopropanol (HFIP) as the solvent for extraction. For this example IV (HFIP)=1.07 dL/g.

Example 2

This example describes the copolymer L-PLA:TMC in a weight ratio of 55:45. Table 1 shows the characterization data for the composition in this example.

Inherent viscosity (IV) was measured using a Cannon MiniPV-HX Automatic Viscometer with hexafluoroisopropanol (HFIP) as the solvent for extraction. For this example IV (HFIP)=1.36 dL/g.

Example 3

This example describes the co-polymer D,L-PLA:TMC in a weight ratio of 50:50. Table 1 shows the characterization data for the composition in this example.

Inherent viscosity was measured using a Cannon MiniPV-HX Automatic Viscometer with chloroform (CHCl3) as the solvent for extraction. For this example IV (CHCl3)=0.933 dL/g and the glass transition for the polymer was determined to be 7.2° C.

Example 4

This example describes the copolymer of L-PLA:TMC in a weight ratio of 75:25. Table 1 shows the characterization data for the composition in this example, in the form of a purified sample and T=150MIN. To obtain the purified sample, the copolymer was dissolved in chloroform (CHCl3) at 2-5 wt. % and precipitated in 10× isopropyl alcohol (IPA), and then dried in vacuo.

Inherent viscosity (IV) was measured using a Cannon MiniPV-HX Automatic Viscometer with hexafluoroisopropanol (HFIP) as the solvent for extraction. For this example IV (HFIP)=1.349 dL/g and the glass transition for the polymer was determined to be 32.95° C.

Example 5

This example is a summary depicting in tabular form, in Table 1, the polymer composition characteristics of Examples 1-4.

TABLE 1

| Sample ID | L-PLA:TMC | L-PLA:TMC | D,L-PLA:TMC | L-PLA:TMC |
|---|---|---|---|---|
| Monomer weight ratio | 55:45 | 55:45 | 50:50 | 75:25 |
| IV (dL/g) | 1.07 | 1.36 | 0.993 | 1.349 |
| Tg (° C.) | | | 7.2 | 32.95 |
| Mn (g/mol) | 23,526 | 25,104 | 40,654 | 40,764 |
| Mw (g/mol) | 66,836 | 76,030 | 56,885 | 91,592 |

TABLE 1-continued

| Sample ID | L-PLA:TMC | L-PLA:TMC | D,L-PLA:TMC | L-PLA:TMC |
|---|---|---|---|---|
| Mz (g/mol) | 97,392 | 111,411 | 69,566 | 132,722 |
| PD | 2.84 | 3.03 | 1.40 | 2.25 |
| Ivw (dL/g) | 0.71 | 0.70 | 0.39 | 0.78 |
| dn/dc | 0.05 | 0.05 | 0.046 | 0.047 |
| Example | 1 | 2 | 3 | 4 |

Example 6

This example describes the solubility characterization of TMC-based polymers in various solvents.

Triacetin, triethyl citrate, triethyl 2-acetylcitrate, tributyl citrate, butyl benzoate, and tributyl O-acetylcitrate were utilized to test the solubility of PLA:TMC copolymers as described in Examples 1 and 2. At room temperature these PLA:TMC copolymers were not soluble in any of the solvents. When the mixtures were heated to 100° C., the copolymers dissolved in triacetin up to 7.5 wt. % of the polymer in the solution. In triethyl citrate and triethyl 2-acetylcitrate, the copolymers dissolved up to 5 wt. % of the polymer in the solution, respectively, when heated to 100° C. The copolymers appeared to be insoluble, or nearly insoluble, in tributyl citrate, butyl benzoate and tributyl O-acetylcitrate even when the mixture were heated to 100° C.

The PLA:TMC copolymers in Examples 3 and 4 were accessed for solubility in triacetin. It was determined that both copolymers were soluble at 7.5 wt. % of the polymer in the solution at room temperature.

Example 7

This example demonstrates the injectability of the formulations of the TMC-polymers described herein.

D,L-PLA:TMC 50:50, as previously described in Example 3, was dissolved in 11 g of triacetin (Sigma-Aldrich, St. Louis) in 25 ml glass vials to obtain approximately a 6% solution by maintaining the mixture on a stir plate with a magnetic stir bar. From this stock solution, formulations containing the addition of various amounts of poly(ethylene glycol) (PEG) (Sigma-Aldrich, St. Louis) with a molecular weight of 400 was added to create solutions of 0 wt. %, 1 wt. %, and 5 wt. % PEG by total weight.

Injection force vs displacement was measured on a TA XT Plus Texture Analyzer at a speed of 200 mm/min using a Schott unsiliconized SyriQ syringe equipped with a 27 G ½ inch thin wall needle with approximately 0.96 µl of solution. The filled syringes were retained for 24 hr before testing to allow sufficient solution contact with syringe stopper.

All force vs displacement data were flat, with approximately the same values near their maximum forces. Data after the maximum force was utilized to determine the average glide force. The average glide force for 0 wt. %, 1 wt. %, and 5 wt. % PEG, respectively, was determined to be 104 N, 103 N, and 98 N. This demonstrated a clear effect of PEG concentration on glide force with increasing PEG reducing the glide force.

Example 8

This example demonstrates the lower injection force for the TMC-based copolymers described herein compared to conventional PLGA polymers.

Resomer® RG 756 S, Poly(D,L-lactide-co-glycolide) purchased from Evonik Industries, Germany, was dissolved in 11 g of triacetin (Sigma-Aldrich, St. Louis) in 25 ml glass vials to obtain approximately a 6% solution by maintaining the mixture on a stir plate with a magnetic stir bar. From this stock solution, formulations containing the addition of various amounts of poly(ethylene glycol) (PEG) (Sigma-Aldrich, St. Louis) with a molecular weight of 400 was added to create solutions of 0 wt. % and 5 wt. % PEG by total weight.

Injection force vs displacement was measured on a TA XT Plus Texture Analyzer (Hamilton, Mass.) at a speed of 200 mm/min using a Schott unsiliconized SyriQ syringe equipped with a 27 G ½ inch thin wall needle with approximately 0.96 µl of solution. The filled syringes were retained for 24 hr before testing to allow sufficient solution contact with syringe stopper.

All force vs displacement data were flat, with approximately the same values near their maximum forces. Data after the maximum force was utilized to determine the average glide force. The average glide force for 0 wt. % and 5 wt. % PEG, respectively, was determined to be 117 N and 113 N. This demonstrated a clear effect of PEG concentration on glide force with increasing PEG reducing the glide force.

Example 9

This example demonstrates the ability of the TMC-based copolymers described herein to be injected as a liquid through a small gauge needle syringe and solidify within a tissue bed as a single mass.

L-PLA:TMC 55:45, as previously described in Example 1, was dissolved in 12 g of triacetin (Sigma-Aldrich, St. Louis) in 25 ml glass vials to obtain an approximately 7.5% solution by maintaining the mixture on a stir plate with a magnetic stir bar and heated to 100° C. From this stock solution, formulations containing the addition of various amounts of poly(ethylene glycol) (PEG) having a molecular weight of 4,500 (Spectrum Chemical MFG Corp. (New Brunswick, N.J.)) were added to create solutions of 1 wt. % and 5 wt. % PEG by total weight. Bovine Serum Albumin (BSA), a model protein bioactive agent, was also formulated with the polymer containing solutions at 1.5 wt. %. Raw BSA powder was ground with a mortar and pestle and sieved using a 45 µm molecular sieve. BSA microparticles were added to the polymer solution at room temperature and then mixed.

Each of the formulations was delivered into the eyes of an animal subject, postmortem, via an intravitreal injection (IVI) of approximately 100 µl. A 27 gauge needle was inserted into the sclera of the superior lateral portion of the eye and the polymer formulation was injected from a 1 ml syringe.

Within hours of injection, the eyes were harvested and each eye was immersed in its own labeled container of Davidson's Solution for a minimum of one hour. After the initial immersion, a small opening with a scalpel was created in the lateral aspect of each eye in order to facilitate thorough fixation of the vitreous body and retina. Additional trimming of intraocular fat and muscle tissue was performed and each eye was re-immersed in Davidson's Solution for 24-48 hours.

Each eye was visually examined with a low power microscope after being bisected to provide a clear view into the vitreous. An opaque globular polymer mass was revealed for each injection, thereby demonstrating that the formulation had solidified and remained as a single mass in the eye.

Example 10

This example demonstrates the ability of the TMC-based copolymers described herein to be injected as a liquid through a small gauge needle syringe, solidify within a tissue bed as a single mass, and exhibit in vivo biocompatibility and tolerability over time.

The copolymer L-PLA:TMC 75:25 as described in Example 4 and D,L-PLA:TMC 50:50 as described in Example 3 were prepared as described in Example 7 to produce 6% polymer solutions with 5 wt. % PEG. Each solution was processed aseptically through a 0.2 µm sterile filter into 1 ml syringes. Each syringe contained approximately 200 µl of formulation.

The polymer formulations were delivered into the eyes of an animal subject and each eye only received a single injection. A 27 gauge needle was inserted into the sclera of the superior lateral portion of the eye and approximately 100 µl of polymer injected. The in-life period of the polymer formulation injections was approximately 30 days. Approximately every week the intraocular pressure (IOP) was measured.

Immediately post-op, the IOP was much higher (greater than 300%) than the baseline for all, as was expected. With the injection, more overall volume has been added to the eye, and thus, increasing IOP. The immediate rise in IOP returned to normal values within approximately 30 min. The polymer formulation was visible within the eye for all of the eyes that received an injection. Approximately every week IOP exams were performed and all of the values were determined to be within normal range. The resolution of the IOP increases, with initial injection, is a level of demonstration of biocompatibility and tolerability.

The eyes were examined and inter ocular pressure (IOP) was obtained. At retrieval, the eyes were gently removed, grossly examined, and fixed in Davidson's Solution for a minimum of 24 hours. Post fixation, the eyes were processed for histological analyses.

Visual examination showed that all the eyes were within normal anatomical considerations with no abnormalities observed. At tissue trimming, rounded aggregates of translucent polymer were identified within the vitreous body.

Microscopically, by examination of histological slides, all evaluated areas of the eyes were within normal limits with no abnormalities observed. During histological processing, much of the vitreous was not preserved and consequently, no direct examination of the polymer formulation system within the vitreous could be made.

Any inflammation within the vitreous humor could not be evaluated/assessed due to loss of the vitreous humor during tissue processing. However, there was not an active and transmigrating inflammatory cell population identified within the retina. Migrating through the retina to get to the vitreous humor would be the pathway of access for inflammatory cells.

Taken together, the findings of this example support an acceptable safety profile, with no risks identified, for the injected polymers in the vitreous body. Overall this is an indication of biocompatibility and tolerability.

Example 11

This example compares the controlled release of a model protein bioactive agent using TMC-based copolymer formulations described herein (containing no PEG) to PLGA formulations (containing no PEG).

In this example, bovine serum albumin (BSA) was obtained from Sigma Life Science (St. Louis, Mo.) as a model protein bioactive agent. The copolymers utilized in this example were L-PLA:TMC 55:45 as described in Example 1 and L-PLA:TMC 55:45 as described in Example 2.

To prepare a L-PLA:TMC polymer stock solution, approximately 1.9 g of L-PLA:TMC polymer of Example 1 was dissolved in 23.2 g of triacetin. This mixture was maintained at approximately 100° C., while stirred, for 2 hrs to obtain a homogenous solution. Raw BSA powder was ground with a mortar and pestle and sieved using a 45 µm sieve. A mass of 0.37 g of sieved BSA microparticles were added to the polymer solution at room temperature and mixed. The final formulation consisted of 7.5 wt. % of polymer and 1.5 wt. % of BSA. Before transferring the formulation into a 1 ml syringe with a 16 gauge needle, the formulation was briefly stirred again to ensure homogeneity. Approximately 50 µl of the formulation was injected into a 13 ml glass test tube containing 3 ml of 1×PBS with 0.01% w/v polysorbate 20 and 0.02% w/v sodium azide. Upon injection, a single depot of the formulation was formed. The weight of the polymer depot was determined by the gravimetric difference between weighing the glass tube before and after formulation injection.

The procedure set forth above was repeated with the L-PLA:TMC of Example 2 to obtain mixtures that consisted of 7.5 wt. % of polymer and 1.5 wt. % of BSA. Before transferring the formulation into a 1 ml syringe with a 16 gauge needle, the formulation was briefly stirred again to ensure homogeneity. Approximately 50 µl of the formulation was injected into a 13 ml glass test tube containing 3 ml of 1×PBS with 0.01% w/v polysorbate 20 and 0.02% w/v sodium azide. Upon injection, a single depot of the formulation was formed. The weight of the polymer depot was determined by the gravimetric difference between weighing the glass tube before and after formulation injection.

Similarly, commercially available PLGA polymers of high molecular weight (RS756S, from Evonik Industries, Germany) and low molecular weight (RS752S from Evonik Industries, Germany) were used as controls. The final formulations consisted of 7.5 wt. % of polymer and 1.5 wt. % of BSA. These formulations were prepared without heating the polymer.

At periodic time periods, the 3 ml of PBS solution was collected, retained, and refreshed. The retained samples were analyzed for BSA content by utilizing the Thermo Scientific (Rockford, Il) Bradford assay kit (prod #23209).

FIG. 1 graphically depicts, over time, the percent cumulative mass of BSA released for formulations containing L-PLA:TMC from Example 1 (solid triangles), L-PLA:TMC from Example 2 (solid circles), and PLGA low MW (RS752S Evonik Industries, Germany) (solid diamonds), and PLGA high MW (RS756S Evonik Industries, Germany) (solid squares). All curves are based on theoretical BSA loading. The PLGA low MW release is a burst system with most of the BSA released the first several weeks, while the PLGA high MW formulation shows an extended biphasic release curve. The L-PLA:TMC formations are both distinct from the PLGA formulations with an initial low level of release followed by a higher level of release. This demonstrates that L-PLA:TMC formulations can produce extend release curves and are different from the PLGA formulations.

Example 12

This example compares the controlled release of a model protein bioactive agent using TMC-based copolymer formulations described herein (containing PEG) to PLGA formulations (containing PEG).

In this example, bovine serum albumin (BSA) was obtained from Sigma Life Science (St. Louis, Mo.) as a model protein bioactive agent. The copolymers utilized in this example were L-PLA:TMC 55:45 as described in Example 1 and L-PLA:TMC 55:45 as described in Example 2. All the formulations in this example contained either 1 wt. % or 5 wt. % PEG.

To prepare a L-PLA:TMC polymer stock solution utilizing the L-PLA:TMC copolymer of Example 1, 1 g of the L-PLA:TMC polymer was dissolved in 12 g of triacetin. The mixture was heated to about 100° C. and stirred for 2 hrs until a homogenous solution was obtained. When the polymer solution was cooled to 50° C., 0.14 g of PEG (Spectrum, Mw=4.6K Da) was added to the polymer solution and stirred until a homogenous solution containing 1 wt. % PEG was obtained. To obtain a polymer solution with 5 wt. % PEG, 0.71 g of PEG (Spectrum, Mw=4.6K Da) was added to the polymer solution and stirred until a homogenous solution was obtained. BSA flakes were ground and sieved using a 45 µm molecular sieve. 0.2 g of BSA microparticles were added to the polymer solution after it cooled down to room temperature. The final mixture contained 7.5 wt. % of polymer, either 1 wt. % or 5 wt. % of PEG, and 1.5 wt. % of BSA. The mixture was stirred again and then loaded into a 1 ml syringe equipped with a 16 gauge needle. About 50 µl of the mixture was injected into a 13 ml glass test tube containing 3 ml of 1×PBS with 0.01% w/v polysorbate 20 and 0.02% w/v sodium azide. A polymer depot was formed in the PBS solution. The weight of the polymer depot was calculated by weighing the glass tube before and after polymer mixture injection.

The procedure set forth above was repeated with the L-PLA:TMC of Example 2 to obtain mixtures that contained 7.5 wt. % of polymer, either 1 wt. % or 5 wt. % of PEG, and 1.5 wt. % of BSA. About 50 µl of the mixture was injected into a 13 ml glass test tube containing 3 ml of 1×PBS with 0.01% w/v polysorbate 20 and 0.02% w/v sodium azide. A polymer depot was formed in the PBS solution. The weight of the polymer depot was calculated by weighing the glass tube before and after polymer mixture injection.

Similarly, commercially available PLGA polymers of high molecular weight (RS756S, from Evonik Industries, Germany) and low molecular weight (RS752S from Evonik Industries, Germany) were used as controls. The final PLGA formulations consisted of 7.5 wt. % of polymer and 1.5 wt. % of BSA. These formulations were prepared without heating the polymer.

Figure 2:
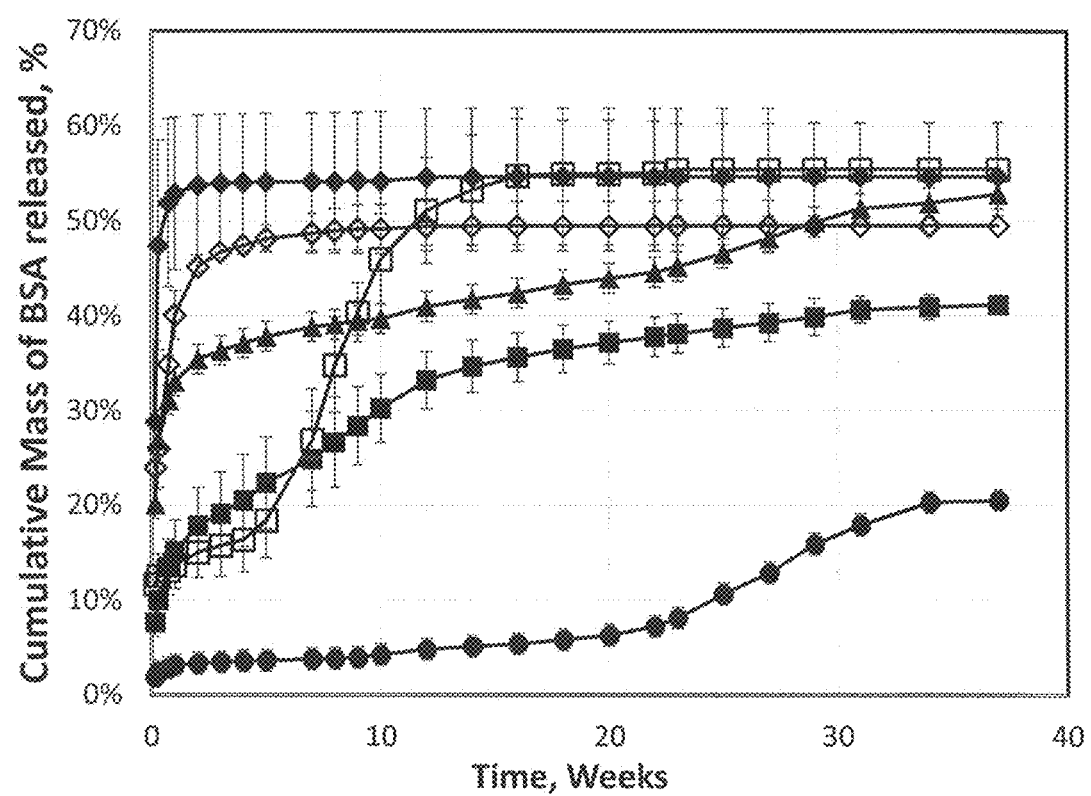
FIG. 2 is a graphical illustration depicting the percent cumulative mass of bovine serum albumin (BSA) that is released over time for the L-PLA:TMC (55:45) formulation of Example 1 with 1 wt. % PEG (solid circles) and 5 wt. % PEG (solid squares), the L-PLA:TMC (55:45) formulation of Example 2 with 1 wt. % PEG (solid diamonds) and 5 wt. % PEG (solid squares), a PLGA high MW formulation (RS756S from Evonik Industries) with 1 wt. % PEG (open squares) and with 5 wt. % PEG (open diamonds). All curves are based on theoretical BSA loading.

At periodic time periods, the 3 ml of PBS solution was collected, retained, and refreshed. The retained samples were analyzed for BSA content by utilizing a Thermo Scientific (Rockford, Il) Bradford assay kit (prod #23209). FIG. 2 graphically depicts the percent cumulative mass of BSA released over time for formulations of L-PLA:TMC (Example 1) with 1 wt. % PEG (solid circles) and 5 wt. % PEG (solid squares); L-PLA:TMC (Example 2) with 1 wt. % PEG (solid triangles) and 5 wt. % PEG (solid diamonds) and PLGA high MW (RS756S, Evonik Industries, Germany) with 1 wt. % PEG (open squares) and 5 wt. % PEG (open diamonds). All curves are based on theoretical loading.

Example 13

This example demonstrates the controlled release of BSA as a model protein bioactive agent from formulations containing a L-PLA:TMC 75:25 polymer (that requires no heating to dissolve) and 0 wt. %, 1 wt. %, 3 wt. % or 5 wt. % of PEG.

A L-PLA:TMC (75:25) polymer solution was prepared by dissolving 1 g of a L-PLA:TMC (75:25) polymer, as described in Example 4, in 12 g triacetin. The mixture was stirred at room temperature for 4 days to get a homogenous solution. While maintaining the L-PLA:TMC polymer solution at 37° C., PEG was added with constant stirring to obtain a formulation with 1 wt. %, 3 wt. % or 5 wt. % of PEG. BSA flakes were ground and sieved using a 45 µm molecular sieve to yield microparticles of BSA. Approximately 0.2 g of BSA microparticles was then added to the above polymer and PEG solution at room temperature. It is to be noted that this procedure was conducted to obtain four separate formulations. The final mixtures contained 7.5 wt. % of polymer, 1.5% BSA, and either 0 wt. % (no PEG addition), 1 wt. %, 3 wt. % or 5 wt. % of PEG.

The mixtures were stirred again and then loaded to a 1 ml syringe equipped with a 16 gauge needle. Approximately 50 µl of mixture was injected into a 13 ml glass test tubes containing 3 ml of 1×PBS with 0.01% w/v polysorbate 20 and 0.02% w/v sodium azide. Polymer depots were formed in the PBS solution. The weight of the polymer depots was calculated by weighing the glass tubes before and after polymer mixture injections.

Figure 3:
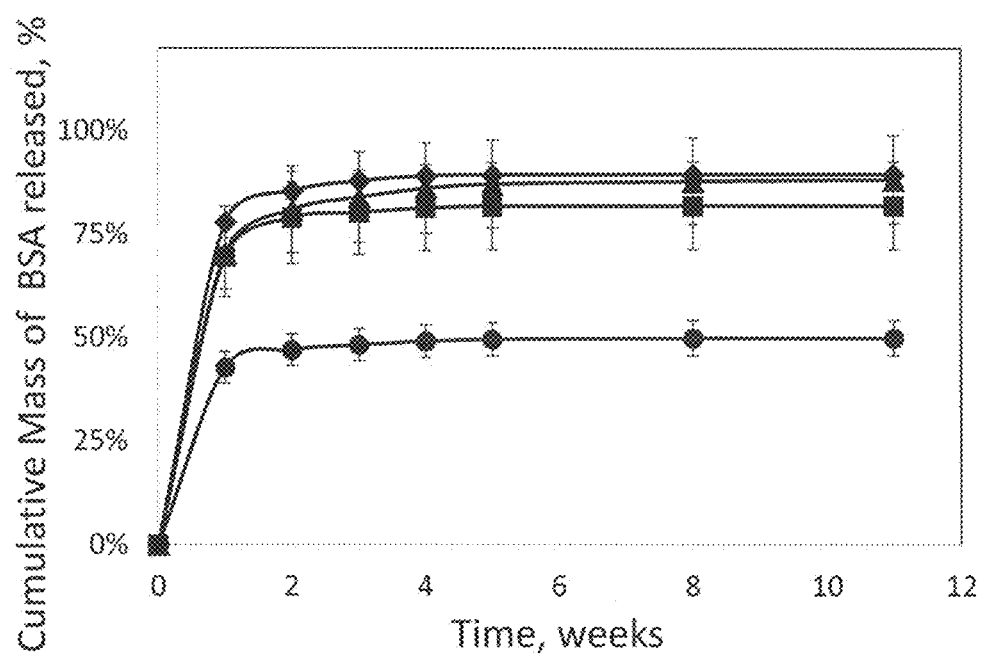
FIG. 3 is a graphical illustration depicting the percent cumulative mass of bovine serum albumin (BSA) that is released over time from L-PLA:TMC 75:25 formulations containing 0 wt. % PEG (solid circles), 1 wt. % PEG (solid squares), 3 wt. % PEG (solid triangles), and 5 wt. % PEG (solid diamonds). All curves are based on theoretical BSA loading.

FIG. 3 graphically depicts the percent cumulative mass of bovine serum albumin (BSA) that is released over time from L-PLA:TMC 75:25 formulations containing 0 wt. % PEG (solid circles), 1 wt. % PEG (solid squares), 3 wt. % PEG (solid triangles), and 5 wt. % PEG (solid diamonds). It was noted that the greater the mass fraction of PEG that was added to the system, the more rapid the BSA is released from polymer depots.

Example 14

This example demonstrates nanoparticles made of copolymers of PLA and TMC as described herein.

Nanoparticles were prepared by dissolving 0.40 g of L-PLA:TMC 75:25 polymer (as described in Example 4) in 20 ml methylene chloride at room temperature. Approximately 40 ml of 5% of polyvinyl alcohol (Aldrich, Mowiol 4-88) aqueous solution was then added to the organic polymer solution. The resultant mixture was sonicated for 2 min using a Branson SXF150 sonifier equipped with a ⅛" tapered probe. Pulse mode with 30 s on and 10 s off was used with 70% of amplitude for sonication to produce an emulsion. Additionally 100 ml of deionized water was added into the emulsion under magnetic stirring at 500 rpm. The emulsion was stirred for about 1 hr and was then treated with rotary evaporation (IKA, RV10 Basic, 100 rpm) under reduced pressure (using a Welch, Dryfast2032 pump) at room temperature for 1 hr to extract the methylene chloride. This resulted in hardened particles that were collected by centrifugation at 4000 rpm for 8 hr (Beckman GS-6KR centrifuge). The particles were re-dispersed in deionized water, to rinse out residual chemicals, and centrifuged again. The supernatant was discarded to remove any remaining polyvinyl alcohol. The cleaned particles were dispersed in 20 ml of deionized water and lyophilized. A scanning electron microscope (SEM) image of the lyophilized particles taken at 20,000× is shown in FIG. 4. The nanoparticles have a spherical shape and are singular.

Example 15

This example demonstrates nanoparticles of copolymers of PLA and TMC contained in an injectable cross-linked PEG system.

Approximately 0.02 g of the L-PLA:TMC 75:25 polymer nanoparticles described in Example 14 were dispersed in 1 ml of 1×PBS and sonicated for 30 s using Branson SXF150 at 70% of amplitude. Additionally 0.2 g of 4-arm PEG amine (Creative PEGWorks, Mw=10K) was dissolved in 0.9 ml of 1×PBS that was adjusted to PH=9.0 with 0.25 N sodium hydroxide solution (Aldrich). Also, 0.04 g of 4-arm PEG succinimidyl glutarate (Creative PEGWorks, Mw=2K) was dissolved in 1 ml of 1×PBS with a PH=4.0 adjusted by 0.1 N hydrochloride acid solution (Aldrich). Approximately 100 µl of the L-PLA:TMC 75:25 nanoparticle dispersion was then added to the PEG-amine solution and mixed well using a magnetic stir bar. The PEG-amine particle solution and PEG-SG solutions were filtered with a 0.2 µm filter (Pall Lifesciences, Acrodisc CR 25 mm syringe filter) separately.

A 2 ml×2 ml 1:1 ratio dual barrel syringe (Plas-Pak Industries Inc.) was then filled with the filtered solutions on separate sides. A modified tip and needle configuration was attached to the dual barrel syringe. The modified tip and needle configuration consisted of a 2 mm×8 mm Element micro-mixer needle tip (Plas-Pak Industries Inc.), with the tapered portion of the tip cut off, a luer lock tip (Qosina, part number 64017) was bonded to the remaining tip segment with super glue, and a 27 G needle was fitted to the luer portion. The solutions were slowly pushed out of the syringe and formed a hydrogel instantaneously with entrapped nanoparticles. Poking the cross-linked gel with a metal spatula demonstrated gel rigidity.

Terpolymer Synthesis

The bioabsorbable polymers identified in the Examples were synthesized according to the methodologies described in "Analysis and characterization of resorbable DL-lactide trimethylene carbonate copolyesters", Journal of Material Science: Materials in Medicine 4(1993) pp. 381-88.

Example 16

This example describes the terpolymer D/L-PLA:TMC:PGA in a weight ratio of 67.5:22.5:10. The PLA to TMC ratio is 3.

Inherent viscosity (IV) was measured using a Cannon MiniPV-HX Automatic Viscometer with chloroform (CHCl3) as the solvent. For this example IV (CHCl3)=1.086 dL/g and the glass transition for the polymer was determined to be −3° C. In vitro degradation studies indicated that the terpolymer essentially degrades over a 6-8 month timeframe.

Example 17

This example describes the terpolymer D/L-PLA:TMC:PGA in a weight ratio of 63.75:21.25:15. The PLA to TMC ratio is 3.

Inherent viscosity (IV) was measured using a Cannon MiniPV-HX Automatic Viscometer with chloroform (CHCl3) as the solvent. For this example IV (CHCl3)=1.155 dL/g and the glass transition for the polymer was determined to be −1° C. In vitro degradation studies indicated that the terpolymer essentially degrades over a 6-8 month timeframe.

Example 18

This example describes the terpolymer D/L-PLA:TMC:PGA in a weight ratio of 45:45:10. The PLA to TMC ratio is 1.

Inherent viscosity was measured using a Cannon MiniPV-HX Automatic Viscometer with chloroform (CHCl3) as the solvent. For this example IV (CHCl3)=1.093 dL/g and the glass transition for the polymer was determined to be 11.3° C. In vitro degradation studies indicated that the terpolymer essentially degrades over a 6-8 month timeframe.

Example 19

This example describes the terpolymer of D/L-PLA:TMC:PHR PGA in a weight ratio of 42.5:42.5:15. The PLA to TMC ratio is 1.

Inherent viscosity (IV) was measured using a Cannon MiniPV-HX Automatic Viscometer with chloroform (CHCl3) as the solvent. For this example IV (CHCl3)=0.9576 dL/g and the glass transition for the polymer was determined to be 13.1° C. In vitro degradation studies indicated that the terpolymer essentially degrades over a 6-8 month timeframe.

Table 2 describes in detail the characterization of the terpolymers used in example 16, 17, 18 and 19.

TABLE 2

| | Terpolymer Characteristics | | | |
|---|---|---|---|---|
| Sample ID | D/L-PLA:TMC:PHR PGA | D/L-PLA:TMC:PHR PGA | D/L-PLA:TMC:PHR PGA | D/L-PLA:TMC:PHR PGA |
| Monomer weight ratio | 67.5:22.5:10 | 63.75:21.25:15 | 45:45:10 | 42.5:42.5:15 |
| IV (dL/g) | 1.086 | 1.155 | 1.093 | 0.9576 |
| Tg (° C.) | −3 | −1 | 11.3 | 13.1 |
| Mn (g/mol) | 31000 | 31000 | 33000 | 34000 |
| Mw (g/mol) | 133000 | 126000 | 103000 | 116000 |
| Mz (g/mol) | 707000 | 620000 | 213000 | 349000 |
| PD | 4.2 | 4.0 | 3.1 | 3.4 |
| dn/dc | 0.057 | 0.056 | 0.052 | 0.052 |
| Example | 16 | 17 | 18 | 19 |

Example 20

This example describes the solubility characterization of TMC-based terpolymers in triacetin organic solvent.

Triacetin was utilized to test the solubility of PLA:TMC:PGA terpolymers as described in Examples 16 and 17 and 18 and 19. At room temperature these PLA:TMC:PGA terpolymers were soluble in triacetin solvent after the polymers were stirred in solvent at room temperature for several days. The terpolymers can be dissolved in triacetin up to 20 wt. % of the polymer in the solution. At 20 wt. %, the solution became too viscous to inject through a 27 G needle.

Example 21

This example demonstrates the injectability of the TMC-terpolymer triacetin solutions described herein. One gram of D,L-PLA:TMC:PGA terpolymer, as previously described in Example 16 and 19 was dissolved in 12 g of triacetin (Sigma-Aldrich, St. Louis) in 25 ml glass vials, respectively, to obtain approximately 7.5 wt. % polymer solutions by maintaining each mixture on a stir plate with a magnetic stir bar. A clear homogenous polymer solution was obtained after the mixture was stirred for a few days at room temperature.

Injection force vs displacement was measured on a TA XT Plus Texture Analyzer at a speed of 200 mm/min using a Schott unsiliconized SyriQ syringe equipped with a 27 G ½ inch thin wall needle with approximately 0.96 µl of solution. The filled syringes were retained for 30 min before testing to allow sufficient solution contact with syringe stopper.

All force vs displacement data were flat, with approximately the same values near their maximum forces. Data after the maximum force was utilized to determine the average glide force. The average glide force for terpolymer in example 16 and 19, respectively, was determined to be 98 N, and 120 N.

Example 22

This example demonstrates the ability of the TMC-based terpolymers described herein in Examples 16, 17, 18, and 19 to be injected as a liquid through a small gauge needle syringe and solidify within a tissue bed as a single mass. This was prepared in accordance with Example 21 to yield a solution.

Each of the formulations was examined at retrieval with a low power microscope after being bisected to provide a clear view into the vitreous. An opaque globular polymer mass was revealed for each injection, thereby demonstrating that the formulation had solidified and remained as a single mass in the eye.

Example 23

This example describes making microparticle protein model protein bioactive agent using spray drying process.

In this example, bovine serum albumin (BSA) was obtained from Sigma Life Science (St. Louis, Mo.) as a model protein bioactive agent.

To prepare BSA microparticles using spray drying process, BSA powder (Sigma 98-99% A-7906 lot no #: 39F0001) was dissolved in di-water at a concentration of 8 wt. %. The solution was spray dried using Buchi Model B-290 mini spray dryer. The inlet temperature was set at 100° C. with 100% aspirator capacity, the rotameter was set at 40 mm height which corresponded to a gas flow of 473 L/hr. Nitrogen was used as spraying air. The peristaltic pump was set at 30%. These resulted in an outlet temperature of 70° C. The spray-dried BSA microparticles (MS-2) was collected in a clean dry glass vial and stored in 4° C. fridge till further use. The particles were examined by SEM, the results showed that they are in the size range of 1-10 um.

Example 24

This example compares the controlled release of a model protein bioactive agent using TMC-based terpolymer formulations described herein containing and 0 wt. %, 1 wt. %, 1.5 wt. %, 2.3% wt., or 3 wt. % of PEG.

In this example, bovine serum albumin (BSA) was obtained from Sigma Life Science (St. Louis, Mo.) as a model protein bioactive agent. The terpolymer utilized in this example were D/L-PLA:TMC:PGA 63.75:21.25:15 as described in Example 17

BSA microparticles was made in accordance to Example 23 using a 1 wt. % of BSA aqueous solution. BSA microparticles were examined by SEM, the results showed that they are in the size range of 1-10 um.

A D/L-PLA:TMC:PGA (63.75:21.25:15) terpolymer solution was prepared by dissolving 1 g of a D/L-PLA:TMC:PGA (63.75:21.25:15) polymer, as described in Example 17, in 12 g triacetin with proper amount of PEG (Sigma, P-3515, Lot 17H0551, Mw=1000) to obtain a formulation with 0 wt. %, 1 wt. %, 1.5 wt. %, 2.3 wt. %, 3 wt. % and 5 wt. % of PEG (Sigma, Mw=1000). The mixture was stirred at room temperature for 4 days to get a homogenous solution. Approximately 0.2 g of BSA microparticles was then added to the above polymer and PEG solution at room temperature. It is to be noted that this procedure was conducted to obtain 5 separate formulations. The final mixtures contained 7.5 wt. % of polymer, 1.5% BSA, and either 0 wt. % (no PEG addition), 1.5 wt. %, 2 wt. %, 2.3 wt. % or 3 wt. % of PEG.

The mixtures were stirred again and then loaded to a 1 ml syringe equipped with a 16 gauge needle. Approximately 100 µl of mixture was injected into a 13 ml glass test tubes containing 3 ml of 1×PBS with 0.01% w/v polysorbate 20 and 0.02% w/v sodium azide. Polymer depots were formed in the PBS solution. The weight of the polymer depots was calculated by weighing the glass tubes before and after polymer mixture injections.

Figure 6:
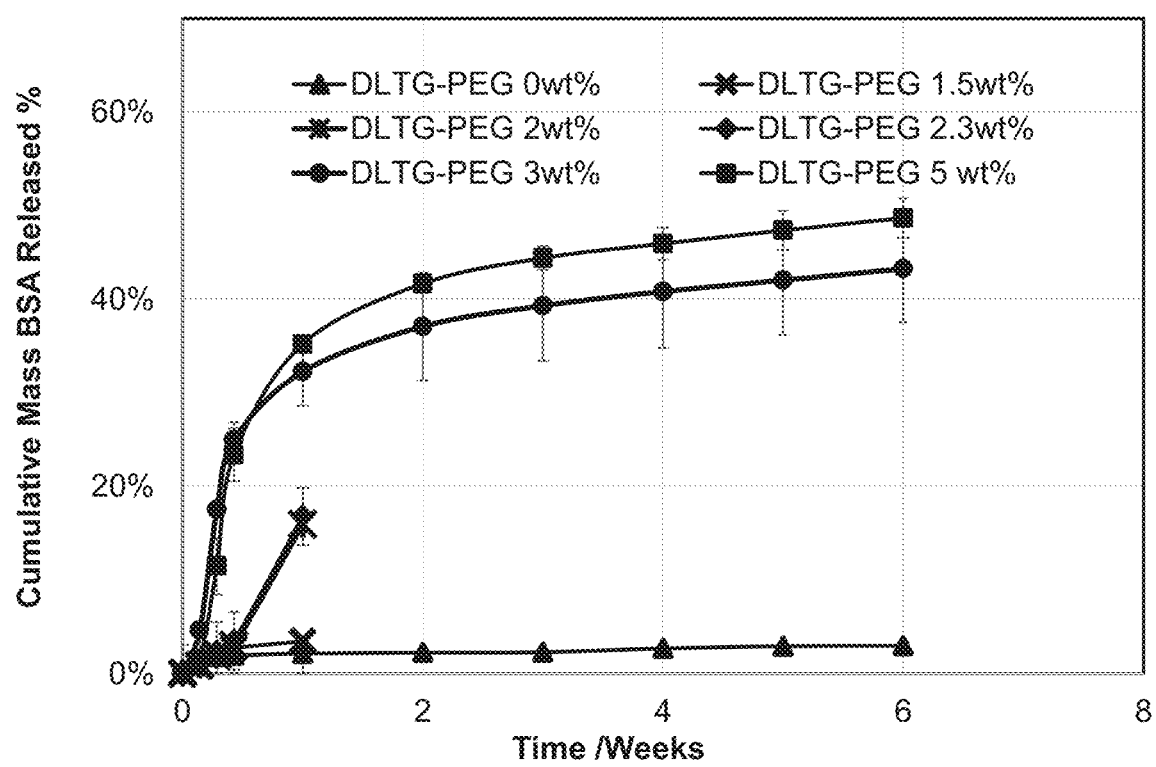
FIG. 6 is a graphical illustration depicting BSA released from a D/L-PLA:TMC:PGA and PEG system.

FIG. 6 graphically depicts the percent cumulative mass of bovine serum albumin (BSA) that is released over time from D/L-PLA:TMC:PGA (63.75:21.25:15) formulations containing 0 wt. % PEG (solid triangles), 1.5 wt. % PEG (cross), 2 wt. % PEG (star), and 2.3 wt. % PEG (solid diamonds), 3 wt. % PEG (solid circles) and 5 wt. % PEG (solid squares). It was noted that when over 3 wt. % of PEG was added to the system, BSA was rapidly released in the first week. When the total amount of PEG was between 1.5-2.3 wt. %, it resulted in a controlled release within the first week.

Example 25

This example compares the controlled release of a model protein bioactive agent using TMC-based terpolymer formulations described herein containing and 0.23 wt. %, 0.38 wt. %, 0.54 wt. %, 1 wt. %, or 1.5 wt. % of Poloxamer F68.

In this example, the terpolymer utilized in this example were D/L-PLA:TMC:PGA 63.75:21.25:15 as described in Example 17. The model protein bioactive agent BSA microparticles was the same as described in Example 24.

A D/L-PLA:TMC:PGA (63.75:21.25:15) terpolymer solution was prepared by dissolving 1 g of a D/L-PLA:TMC:PGA (63.75:21.25:15) polymer, as described in Example 21, in 12 g triacetin with proper amount of Poloxamer F68 (BASF, Lutrol Micro 68 MP, Lot #W045740, Mw=8400) to obtain a formulation with 0.23 wt. %, 0.38 wt. %, 0.54 wt. %, 1 wt. %, or 1.5 wt. % of Poloxamer. The mixture was stirred at room temperature for 4 days to get a homogenous solution. Approximately 0.2 g of BSA microparticles was then added to the above polymer and PEG solution at room temperature. It is to be noted that this procedure was conducted to obtain 5 separate formulations. The final mixtures contained 7.5 wt. % of polymer, 1.5% BSA, and either 0.23 wt. %, 0.38 wt. %, 0.54 wt. %, 1 wt. %, or 1.5 wt. % of Poloxamer F68.

The mixtures were stirred again and then loaded to a 1 ml syringe equipped with a 16 gauge needle. Approximately 100 µl of mixture was injected into a 13 ml glass test tubes containing 3 ml of 1×PBS with 0.01% w/v polysorbate 20 and 0.02% w/v sodium azide. Polymer depots were formed in the PBS solution. The weight of the polymer depots was calculated by weighing the glass tubes before and after polymer mixture injections.

Figure 7:
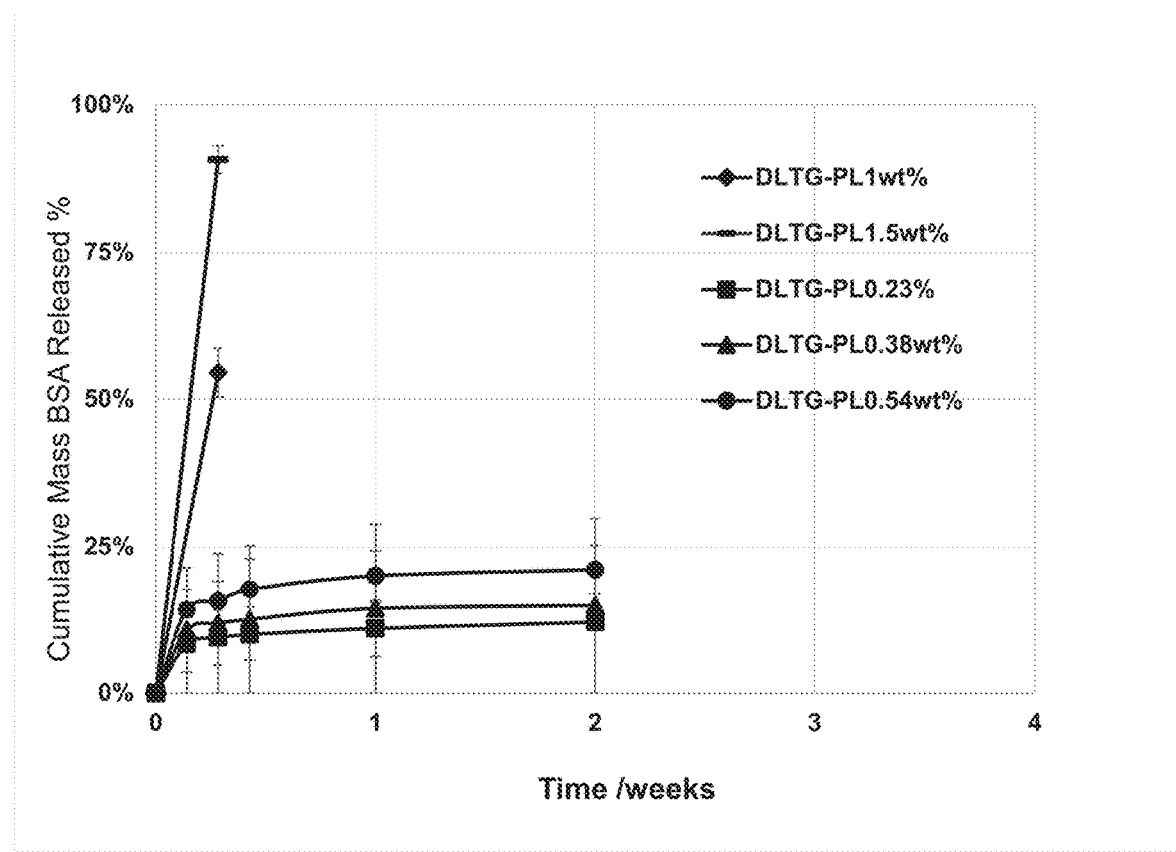
FIG. 7 is a graphical illustration depicting BSA release profiles from DLTG/Polozemar systems.

FIG. 7 graphically depicts the percent cumulative mass of bovine serum albumin (BSA) that is released over time from D/L-PLA:TMC:PGA (63.75:21.25:15) formulations containing 0.23 wt. % of Poloxamer (solid squares), 0.38 wt. % Poloxamer (solid triangles), 0.54 wt. % Poloxamer (solid circle), and 1 wt. % Poloxamer (solid diamonds), 1.5 wt. %

Poloxamer (solid rectangles). It was noted that when more than 1 wt. % of Poloxamer was added to the system, it resulted in burst release of BSA in the first few days and 80% to 90% of BSA was gone within a week. When the amount of Poloxamer was between 0.2-0.5 wt. %, it resulted in a sustained release within the first week without massive burst release of BSA.

Example 26

This example compares the controlled release of a model protein bioactive agent using TMC-based copolymer and terpolymer blend formulations described herein In this example, the terpolymer utilized in this example was D/L-PLA:TMC:PGA 63.75:21.25:15 as described in Example 17. The copolymer utilized in this example was L-PLA-TMC 75:25 as described in Example 4. The model protein bioactive agent BSA microparticles was the same as describe in Example 24.

A D/L-PLA:TMC:PGA (63.75:21.25:15) terpolymer and L-PLA:TMC 75:25 copolymer blend solution was prepared by dissolving a total amount of 1 g of a D/L-PLA:TMC:PGA (63.75:21.25:15) polymer, as described in Example 17, and a L-PLA-TMC 75:25 as described in Example 4, in 12 g triacetin to obtain a formulation with 0 wt. %, 25 wt. %, 50 wt. %, 75%, or 100 wt. % of L-PLA:TMC 75:25 polymer solution. The mixture was stirred at room temperature for 4 days to get a homogenous solution. Approximately 0.2 g of BSA microparticles was then added to the above polymer solution at room temperature. It is to be noted that this procedure was conducted to obtain 5 separate formulations. The final mixtures contained 7.5 wt. % of polymer blend, 1.5% BSA, and either 0 wt. %, 25 wt. %, 50 wt. %, 75 wt. %, or 100 wt. % of L-PLA:TMC 75:25.

The mixtures were stirred again and then loaded to a 1 ml syringe equipped with a 16 gauge needle. Approximately 100 μl of mixture was injected into a 13 ml glass test tubes containing 3 ml of 1×PBS with 0.01% w/v polysorbate 20 and 0.02% w/v sodium azide. Polymer depots were formed in the PBS solution. The weight of the polymer depots was calculated by weighing the glass tubes before and after polymer mixture injections.

Figure 8:
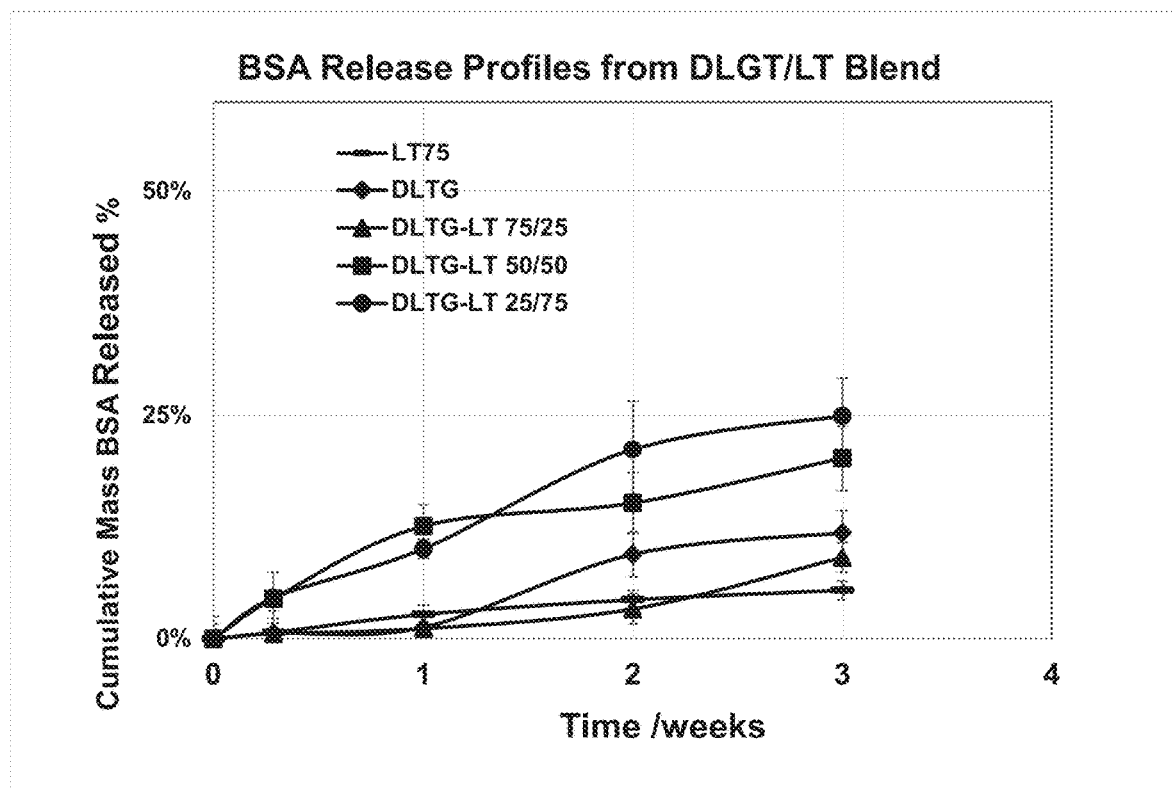
FIG. 8 is a graphical illustration depicting BSA released from D/L-PLA:TMC:PGA and L-PLA:TMC blends.

FIG. 8 graphically depicts the percent cumulative mass of bovine serum albumin (BSA) that is released over time from D/L-PLA:TMC:PGA (63.75:21.25:15) terpolymer (solid diamonds), L-PLA:TMC 75:25 copolymer (rectangles), and polymer blend formulations containing 25 wt. % of L-PLA:TMC 75:25 (solid triangles), 50 wt. % of L-PLA:TMC 75:25 (solid squares), 75 wt. % of L-PLA:TMC 75:25 (solid circles). It was noted that when more than 50 wt. % of the copolymer L-PLA:TMC 75:25 as described in example 4 was used in the blend, a sustained BSA release was observed in the first 2 weeks.

Example 27

BSA Encapsulated LT75 Microspheres

This example demonstrates BSA encapsulated microspheres made of copolymers of PLA and TMC as described herein.

Figure 5:
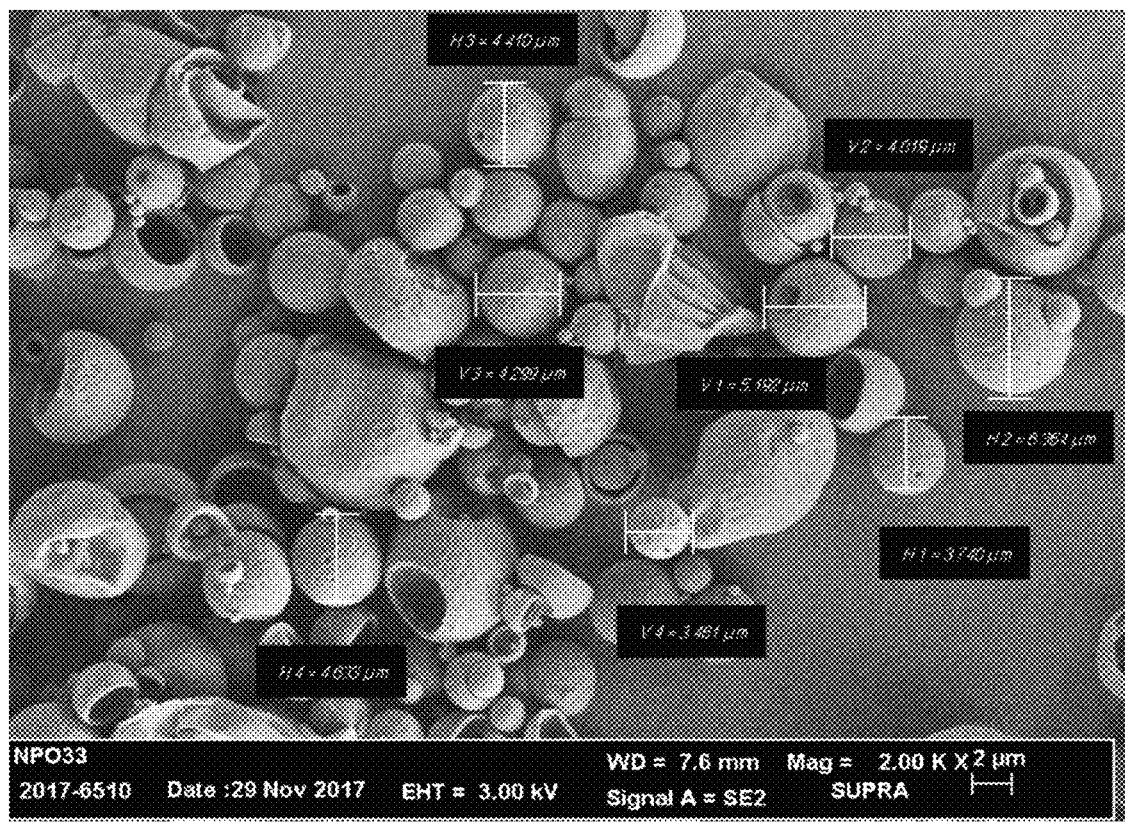
FIG. 5 is a scanning electron micrograph of BSA encapsulated microspheres, taken at 20,000×.

BSA encapsulated microspheres were prepared by dissolving 0.50 g of L-PLA:TMC 75:25 polymer (as described in Example 4) in 15 ml methylene chloride at room temperature. 1 g BSA was dissolved in 10 mL of 1×PBS solution to make a BSA solution with a concentration of 100 mg/mL. 1.5 mL of the 100 mg/mL BSA solution was then added to the organic polymer solution. The resultant mixture was sonicated for 2 min using a Branson SXF150 sonifier equipped with a ⅛" tapered probe. Pulse mode with 30 s on and 10 s off was used with 50% of amplitude for sonication to produce a water-in-oil emulsion. Approximately 150 mL of 5% of polyvinyl alcohol (Aldrich, Mowiol 4-88) aqueous solution was then added to the emulsion. The resultant mixture was homogenized at 5000 rpm for 2 min using an IKA T18 digital homogenizer. Additionally 1 L of deionized water was added into the emulsion under magnetic stirring at 500 rpm. The emulsion was stirred for about 1 hr and was then treated with rotary evaporation (IKA, RV10 Basic, 100 rpm) under reduced pressure (using a Welch, Dryfast2032 pump) at room temperature for 1 hr to remove methylene chloride. The emulsion was centrifuged, the supernatant was discarded to remove any remaining polyvinyl alcohol. The particles were re-dispersed in di-water and centrifuged again. The cleaned particles were dispersed in 20 ml of deionized water and lyophilized. A scanning electron microscope (SEM) image of the lyophilized particles taken at 20,000× is shown in FIG. 5.

BSA encapsulation efficiency and loading amount were examined by extracting BSA from lyophilized microspheres using methylene chloride and THF (1:1 volume ratio) once and then THF twice, followed by petroleum ether. Extracted BSA was air dried and then dissolved in PBS. BSA amount was tested by Bradford Assay. The encapsulation efficiency of the particles was 22% and the loading of BSA was 6.4 wt. %.

Example 28

This example demonstrates the injectability of the formulations of the BSA encapsulated TMC-copolymer microparticles with PEG described herein. 0.04 G of Poly(ethylene oxide), 4-arm, succinimidyl glutarate terminated (PEG-SG) having a molecular weight of 2 KDa (Creative PEGWorks) and 0.2 G of Poly(ethylene oxide), 4-arm, amine terminated (PEG-AM) having a molecular weight of 10 KDa (Creative PEGWorks) were weighted into two clean glass vials, respectively. 0.01 g of BSA encapsulated D,L-PLA:TMC 75:25 microparticles prepared as described in Examples 27 was weighted into a third clean vial. All vials were capped with a thread cap with rubber septa. The vials were then degassed with nitrogen for 30 s and sealed. PEG and nanoparticle samples were sterilized by Gamma radiation at a dosage of 9-11 kGy. 1 ml of 1×PBS with a pH=4.5 adjusted by 0.1 N hydrochloride acid solution (Aldrich) (PBS 4.5) was injected into PEG-SG vial to make a 4 wt. % PEG-SG solution. 1 ml of 1×PBS that was adjusted to PH=9.0 with 0.25 N sodium hydroxide solution (Aldrich). (PBS 9.0) was injected into PLA-TMC nanoparticle vial to disperse nanoparticles. 0.5 mL of PBS 9.0 was injected into PEG-AM vial to dissolve PEG-AM. After a clear solution of PEG-AM was obtained, 0.5 ml of well dispersed PLA-TMC/PBS 9.0 dispersion was transferred into PEG-AM/PBS 9.0 solution to make a 20% PEG-AM solution with 10 mg/mL of PLA-TMC microparticles. Two 1 ml syringes were then filled with PEG-SG solution and PEG-AM/nanoparticle dispersion, respectively. Each syringe contained approximately 200 μl of PEG formulations. These syringes was assembled to a duel syringe holder (Baxter). A dual syringe tip was attached to the two syringes, and a 27 G needle was fitted to the syringe tip. The solutions were slowly pushed out of the syringe and formed a hydrogel instantaneously with entrapped nanoparticles. Poking the cross-linked gel with a metal spatula demonstrated gel rigidity.

Example 29

PEG-Am and PEG-SG solutions prepared as described in Example 28 were loaded into two 3 ml syringe separately and put on Baxter dual syringe holder. Injection force vs displacement was measured on a TA XT Plus Texture Analyzer at a speed of 200 mm/min using a Baxter dual syringe kit equipped with a 27 G ½ inch thin wall needle with approximately 0.96 μl of solution.

All force vs displacement data were flat, with approximately the same values near their maximum forces. Data after the maximum force was utilized to determine the average glide force. The average glide force for crosslinkable PEG gel in example 28 was determined to be 79 N.

Example 30

This example demonstrates BSA elution from BSA encapsulated microsphere of copolymers of PLA and TMC and from the microsphere contained in an injectable cross-linked PEG system.

Approximately 10 mg of the BSA encapsulated L-PLA:TMC 75:25 polymer microspheres described in Example 27 were dispersed in 1.5 ml of 1×PBS in a 2 mL centrifuge tube (Spin-X® Centrifuge Tube Filters, Corning®). Particles were well dispersed in PBS solution after the mixture was shaken for 1 min using a Vortex. Samples were then incubated in a 37 C degree water bath.

Approximately 5 mg of the BSA encapsulated L-PLA:TMC 75:25 polymer microspheres described in Example 27 were dispersed in 0.5 ml of 1×PBS that was adjusted to PH=9.0 with 0.25 N sodium hydroxide solution (Aldrich). Additionally 0.2 g of 4-arm PEG amine (Creative PEG-Works, Mw=10K) was dissolved in 0.5 ml of 1×PBS that was also adjusted to pH=9.0. The BSA encapsulated L-PLA:TMC 75:25 microsphere dispersion was then added to the PEG-amine solution and mixed well using a magnetic stir bar. 0.04 g of 4-arm PEG succinimidyl glutarate (Creative PEGWorks, Mw=2K) was dissolved in 1 ml of 1×PBS with a PH=4.0 adjusted by 0.1 N hydrochloride acid solution (Aldrich).

Two 1 ml syringes (BD) were assembled into a 1:1 ratio dual syringe holder (Baxter), which were then filled with particles/PEG-amine and PEG-SG solutions on separate sides. A dual syringe tip (Baxter) was attached to the dual barrel syringe and a 27 G needle was fitted to the luer portion. 100 uL of solutions were slowly pushed out of the syringe and formed a hydrogel instantaneously with entrapped microspheres in 2 mL centrifuge tubes (Spin-X® Centrifuge Tube Filters, Corning®) containing 1.5 mL 1×PBS. The centrifuge tubes were incubated in a 37 C degree water bath.

Figure 9:
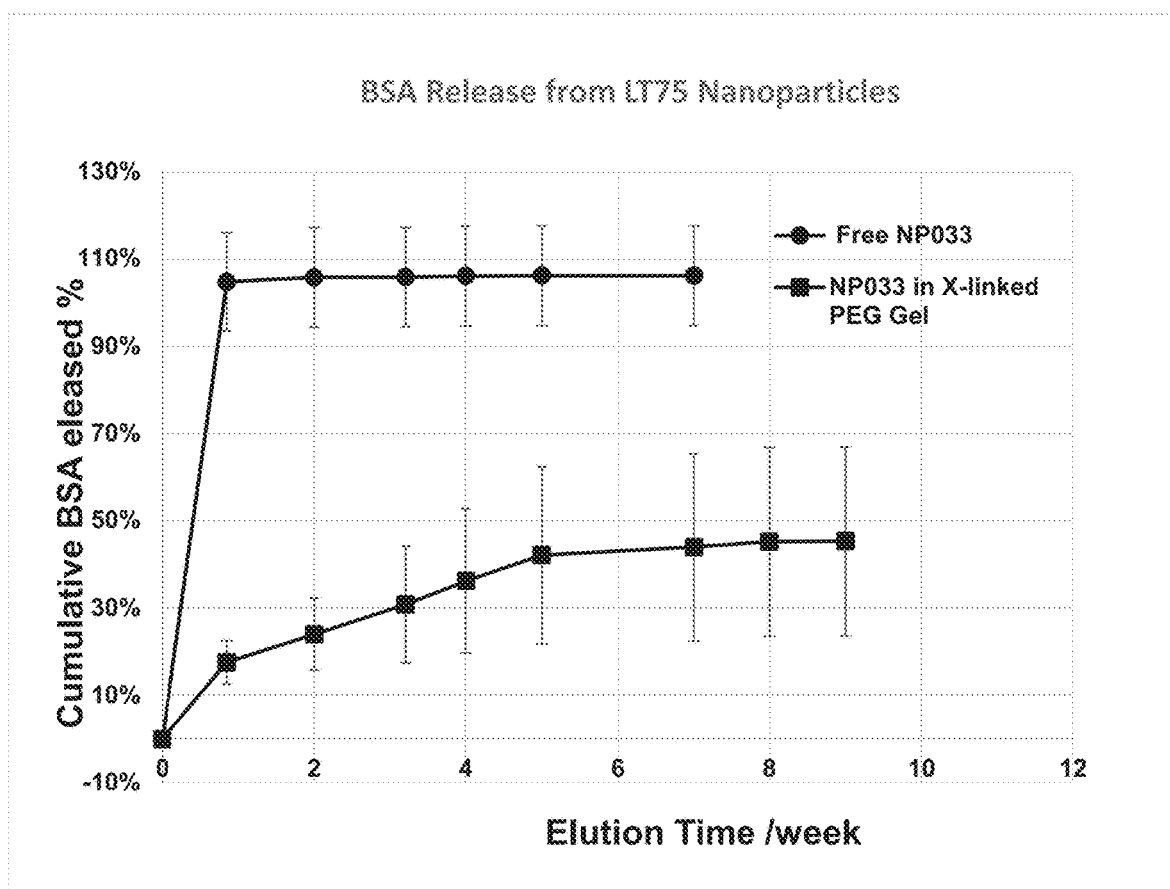
FIG. 9 is a graphical illustration depicting PEG microparticle elution.

FIG. 9 shows BSA elution of free BSA encapsulated microspheres and the particles contained in the cross-linked PEG gels.

Example 31

This example demonstrates the ability of the PLGA-based copolymers to be injected as a liquid through a small gauge needle syringe, solidify within a tissue bed as a single mass, and exhibit some degree of inflammatory reaction.

The copolymer PLA:GA Resomer® RG 756 S, Poly(D,L-lactide-co-glycolide) purchased from Evonik Industries, Germany, was dissolved in 11 g of triacetin (Sigma-Aldrich, St. Louis) in 25 ml glass vials to obtain approximately a 6% solution by maintaining the mixture on a stir plate with a magnetic stir bar. The molecular weight was 76,000 for the PLGA polymer. The solution was processed aseptically through a 0.2 μm sterile filter into 1 ml syringes. Each syringe contained approximately 200 μl of formulation.

The polymer formulations were delivered into the eyes of an animal subject and each eye only received a single injection. A 27 gauge needle was inserted into the sclera of the superior lateral portion of the eye and approximately 100 μl of polymer injected. The in-life period of the polymer formulation injections was approximately 90 days. Approximately every week the intraocular pressure (IOP) was measured.

Figure 10:
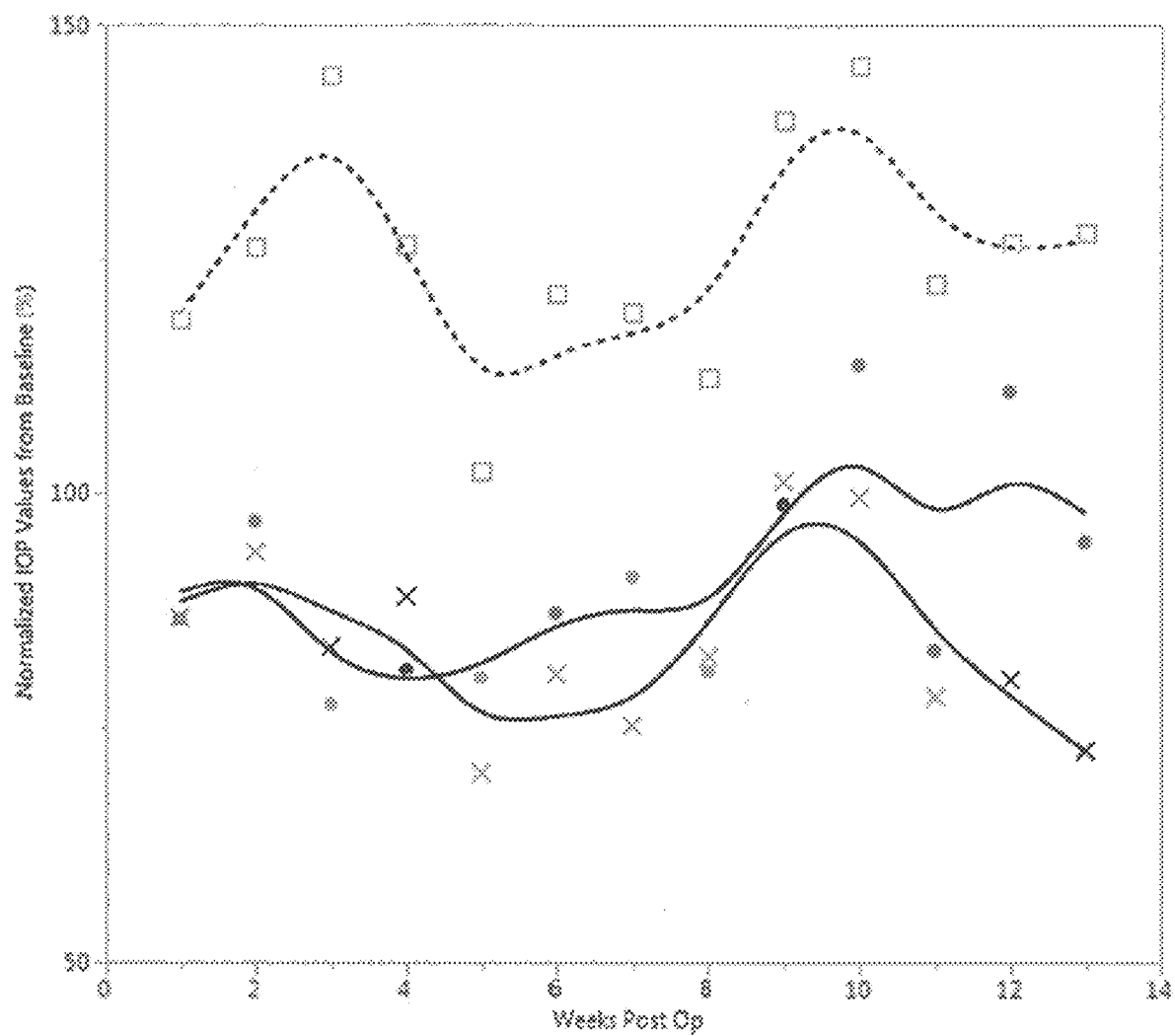
FIG. 10 is a graphical illustration depicting a normalized average IOP over 90 days implant for PLGA, PLA:TMC:PLGA, and cross-linked PEG with PLA:TMC.

Immediately post-op, the IOP was much higher than the baseline for all, as was expected. With the injection, more overall volume has been added to the eye, and thus, increasing IOP. The immediate rise in IOP returned to normal values within approximately 30 min. The polymer formulation was visible within the eye for all of the eyes that received an injection. Approximately every week IOP exams were performed and average normalized values, relative to baseline before implantation, are depicted graphically in FIG. 10 (unfilled square). The dashed curve fitted line indicated a general increase in IOP for the PLAG group as well as the data points being above 100%. Furthermore, visual inspection with an ophthalmoscope revealed redness of the retina, a sign of inflammation, in one observation.

At retrieval, the eyes were examined and inter ocular pressure (IOP) was obtained. The eyes were gently removed, examined, and fixed in Davidson's Solution for a minimum of 24 hours. Post fixation, the eyes were processed for histological analyses.

The tissue samples were processed to yield histological slides and were examined under microscope for inflammation. Examination revealed inflammation.

Taken together, the findings of this example support increased inflammation in the PLGA samples as evidenced by increased IOP above baseline, redness of the retina, and histological tissue reaction.

Example 32

This example demonstrates the ability of TMC-based terpolymers described herein to be injected as a liquid through a small gauge needle syringe, solidify within a tissue bed as a single mass, and exhibit in vivo biocompatibility and tolerability over time.

The terpolymer D/L-PLA:TMC:PGA in a weight ratio of 63.75:21.25:15, described in Example 17, was prepared in a working formulation as described in Example 21. The solution was processed aseptically through a 0.2 μm sterile filter into 1 ml syringes. Each syringe contained approximately 200 μl of formulation.

The polymer formulations were delivered into the eyes of an animal subject and each eye only received a single injection. A 27 gauge needle was inserted into the sclera of the superior lateral portion of the eye and approximately 100 μl of polymer injected. The in-life period of the polymer formulation injections was approximately 90 days. Approximately every week the intraocular pressure (IOP) was measured.

Immediately post-op, the IOP was much higher than the baseline for all, as was expected, as with the injection, more overall volume was added to the eye, and thus, increasing IOP. The immediate rise in IOP returned to normal values within approximately 30 min. The polymer formulation was visible within the eye for all of the eyes that received an injection. Approximately every week IOP exams were performed and average normalized values, relative to baseline before implantation, are depicted graphically in FIG. 10 (solid circle). The resolution of the IOP increased, with initial injection, and maintenance of IOP values at or below 100% was a level of demonstration of biocompatibility and tolerability. Furthermore, visual inspection with an ophthalmoscope revealed no redness of the retina, a possible sign of inflammation if observed, in any observations.

The eyes were examined a final time, and inter ocular pressure (IOP) was obtained. At retrieval, the eyes were removed, examined, and fixed in Davidson's Solution for a minimum of 24 hours. Post fixation, the eyes were processed for histological analyses.

Visual examination showed that all the eyes were within normal anatomical considerations with no abnormalities observed. Round aggregates of the translucent polymer were identified within the vitreous body.

Microscopically, by examination of histological slides, all evaluated areas of the eyes were undertaken. Around the polymer implant (i.e., the solid gel structure) no inflammation was noted.

Taken together, the findings of this example support an acceptable safety profile, with no risks identified, for the injected polymers in the vitreous body. Overall this is an indication of biocompatibility and tolerability with no signs of inflammation.

Example 33

This example demonstrates the ability of the TMC-based polymer nanoparticles with a cross-linkable PEG described herein to be injected as a liquid through a small gauge needle syringe, solidified within a tissue bed as a cross-linked hydrogel containing TMC nanoparticles, and then exhibit in vivo biocompatibility and tolerability over time.

The cross-linkable PEG solutions containing injectable PLA-TMC nanoparticles were prepared as described in Example 28 to yield a sterile formulation.

The formulations were delivered into the eyes of animal subjects and each eye only received a single injection. A 27 gauge needle was inserted into the sclera of the superior lateral portion of the eye and approximately 100 µl of PEG solution were injected. The in-life period of the polymer formulation injections was approximately 90 days. Approximately every week the intraocular pressure (IOP) was measured.

Immediately post-op, the IOP was much higher than the baseline for all, as was expected. With the injection, more overall volume has been added to the eye, and thus, increasing IOP. The immediate rise in IOP returned to normal values within approximately 30 min. The polymer formulation was visible within the eye for all of the eyes that received an injection. Approximately every week IOP exams were performed and average normalized values, relative to baseline before implantation, are depicted graphically in FIG. 10 (shown as X). The maintenance of IOP values at or below 100% is a level of demonstration of biocompatibility and tolerability. Furthermore, visual inspection with an ophthalmoscope revealed no redness of the retina, a possible sign of inflammation if observed, in any observations.

After retrieval, the eyes were examined and inter ocular pressure (IOP) was obtained. The eyes were removed, examined, and fixed in Davidson's Solution for a minimum of 24 hours. Post fixation, the eyes were processed for histological analyses.

Microscopically, by examination of histological slides, all evaluated areas of the eyes were undertaken. Around the implant minimal inflammation was noted.

Taken together, the findings of this example support an acceptable safety profile, with no risks identified, for the injected polymers in the vitreous body. Overall this is an indication of biocompatibility and tolerability with minimal inflammation.

Example 34

This example demonstrates the ability of the TMC-based copolymer L-PLA:TMC 75:25 as described in Example 4 and the terpolymers described herein in Examples 21 to be injected as a liquid through a small gauge needle syringe and solidify within a tissue bed as a single mass. Tissue beds examined in this example were the kidneys, liver, and heart. The solution was prepared in accordance with Example 12 and 21.

Each of the formulations was delivered into the target tissue bed, postmortem, via an intravitreal injection (IVI) of approximately 100 µl. A 27 gauge needle was inserted into the cranial and caudal poles of the left and right kidneys (four foci), 100 uL into the liver (one focus), and 100 uL into the apex of the heart (one focus) was injected from a 1 ml syringe.

Within hours of injection, the tissues were harvested and each was immersed in its own labeled container of Davidson's Solution for a period longer than 24 hrs.

Each tissue bed was visually examined with a low power microscope after being bisected. An opaque globular solid gel mass was revealed for each injection, thereby demonstrating that the formulation had solidified and remained as a single mass.

The invention of this application has been described above both generically and with regard to specific embodiments. It will be apparent to those skilled in the art that various modifications and variations can be made in the embodiments without departing from the scope of the disclosure. Thus, it is intended that the embodiments cover the modifications and variations of this invention provided they come within the scope of the appended claims and their equivalents.

What is claimed is:

1. An injectable sustained-release formulation comprising:
   an injectable bioabsorbable polymer comprising
      a polylactide (PLA), trimethylene carbonate (TMC), polyglycolic acid, (PGA) terpolymer, wherein the terpolymer comprises from 3-19 wt. % PGA and wherein the PLA:TMC weight ratio is from 3.25:1 to 0.75:1;
   a pharmaceutically acceptable excipient;
   at least one solvent selected from 1,2 3-triacetoxypropane, acetyltributyl citrate, triethyl citrate, tributyl citrate, and acetyl triethyl citrate; and
   a bioactive agent;
   wherein said terpolymer is in the form of an injectable liquid;
   wherein the injectable liquid solidifies in a tissue bed in the form of a solid mass,
   wherein the tissue bed is an eye, and
   wherein said formulation is configured to maintain a normalized average intraocular pressure (IOP) in the eye at or below 100% for 14 weeks.

2. The injectable formulation of claim 1, wherein the bioactive agent is incorporated in said injectable bioabsorbable polymer and said bioactive agent has a half-life of release from said injectable bioabsorbable polymer of greater than 30 days.

3. The injectable formulation of claim 1, wherein said excipient is selected from polyethylene glycol, poloxamers, and polyvinyl alcohol.

4. The injectable formulation of claim 1, wherein said terpolymer has a number average molecular weight from 25,000 to 40,000 g/mol.

5. The injectable formulation of claim 1, wherein the bioactive agent is incorporated in said injectable bioabsorbable polymer.

6. The injectable formulation of claim 1, wherein the injectable sustained-release formulation is a delayed-release formulation in vivo or in situ.

7. The formulation of claim 1, wherein said solid mass allows for delayed release of the bioactive agent.

8. The injectable formulation of claim 1, wherein said formulation is used to treat ocular diseases.

9. An injectable sustained-release formulation comprising:
  a first portion comprising nanoparticles formed from a copolymer of polylactic acid (PLA) and trimethylene carbonate (TMC) in an injectable cross-linkable polyethylene glycol (PEG), wherein the first portion is contained within a first barrel of a syringe, and
  a second portion comprising a cross-linkable polyethylene glycol (PEG) contained within a second barrel of the syringe; and
  a bioactive agent encapsulated in said nanoparticles of said first portion,
  wherein said copolymer comprises from 60 to 90 wt. % PLA and from 10 to 40 wt. % TMC,
  wherein the first and second barrels are configured to inject the first and second portions into an eye
  wherein the first portion and the second portion are configured to mix and solidify as a rigid hydrogel with the nanoparticles entrapped therein in the eye, and
  wherein said formulation is configured to maintain a normalized average intraocular pressure (IOP) in the eye at or below 100% for 14 weeks.

10. The injectable formulation of claim 9, wherein said bioactive agent has a half life of release from said nanoparticles of greater than 30 days.

11. The injectable formulation of claim 9, wherein the injectable sustained-release formulation is a delayed-release formulation in vivo or in situ.

12. An injectable sustained-release formulation comprising:
  a first portion comprising nanoparticles formed from a copolymer of polylactic acid (PLA) and trimethylene carbonate (TMC) in an injectable cross-linkable polyethylene glycol (PEG), the first portion contained within a first barrel of a syringe
  a second portion comprising a cross-linkable polyethylene glycol, the second portion contained within a second barrel of the syringe; and
  a bioactive agent encapsulated in said nanoparticles of said first portion,
  wherein the first and second barrels are configured to inject the first and second portions simultaneously or nearly simultaneously,
  wherein a combination of the first portion and the second portion in a tissue bed forms a rigid hydrogel with the nanoparticle entrapped therein,
  wherein the tissue bed is an eye, and
  wherein said formulation is configured to maintain a normalized average intraocular pressure (IOP) in the eye at or below 100% for 14 weeks.

13. The injectable formulation of claim 12, wherein said bioactive agent has a half life of release from said nanoparticles of greater than 30 days.

14. The injectable formulation of claim 12, wherein the injectable sustained-release formulation is a delayed-release formulation in vivo or in situ.

15. The injectable formulation of claim 12, wherein the cross-linkable polyethylene glycol of the first portion comprises a polyethylene glycol amine and the cross-linkable polyethylene glycol of the second portion comprises a polyethylene glycol succinimidyl glutarate.

16. An injectable sustained-release formulation comprising:
  an injectable bioabsorbable polymer comprising
    a D/L-polylactide (D/L-PLA), trimethylene carbonate (TMC), and polyglycolic acid (PGA) terpolymer, wherein the terpolymer comprises from 3-19 wt. % PGA and wherein the D/L-PLA:TMC weight ratio is from 3.25:1 to 0.75:1;
  a pharmaceutically acceptable excipient;
  a solvent; and
  a bioactive agent,
  wherein the injectable bioabsorbable polymer solidifies in a tissue bed in the form of a solid mass,
  wherein the tissue bed is an eye, and
  wherein said formulation is configured to maintain a normalized average intraocular pressure (IOP) in the eye at or below 100% for 14 weeks.

17. The injectable formulation of claim 16, wherein the solvent comprises 1,2,3-triacetoxypropane, acetyltributyl citrate, triethyl citrate, tributyl citrate, or acetyl triethyl citrate.

* * * * *